(12) United States Patent
Hirai

(10) Patent No.: US 8,206,410 B2
(45) Date of Patent: Jun. 26, 2012

(54) SURGICAL OPERATING APPARATUS

(75) Inventor: Yuji Hirai, Hachioji (JP)

(73) Assignee: Olympus Medical Systems Corp. (JP)

( * ) Notice: Subject to any disclaimer, the term of this patent is extended or adjusted under 35 U.S.C. 154(b) by 1122 days.

(21) Appl. No.: 12/059,322

(22) Filed: Mar. 31, 2008

(65) Prior Publication Data

US 2009/0275864 A1  Nov. 5, 2009

(51) Int. Cl.
*A61B 17/32* (2006.01)
(52) U.S. Cl. ...................................... 606/169
(58) Field of Classification Search .................... 606/41, 606/169, 39, 167, 190, 205, 127, 128, 159, 606/170, 171, 180, 166; 601/2, 3; 604/22, 604/20, 21, 501; 128/200.16; 433/86, 119; 600/437, 459, 439, 471
See application file for complete search history.

(56) References Cited

U.S. PATENT DOCUMENTS

| 7,766,929 B2 * | 8/2010 | Masuda .......................... 606/169 |
| 2002/0057541 A1 | 5/2002 | Donofrio | |
| 2009/0088785 A1 * | 4/2009 | Masuda .......................... 606/169 |
| 2009/0248050 A1 * | 10/2009 | Hirai .............................. 606/169 |
| 2009/0248051 A1 * | 10/2009 | Masuda .......................... 606/169 |

FOREIGN PATENT DOCUMENTS

| EP | 0947167 A1 * | 6/1999 |
| JP | 2003-339731 | 12/2003 |
| JP | 2004-154331 | 6/2004 |

OTHER PUBLICATIONS

European Search Report dated Jun. 10, 2009 in counterpart European Patent Application No. EP 09 00 4454 (English language).
Letter from German associate dated Jun. 17, 2009 forwarding the European Search Report dated Jun. 10, 2009 to Japanese associate, including discussion of relevancy thereof (English language). German associate's letter dated Jun. 17, 2009 was date stamped received by Japanese associate on Jun. 29, 2009.

\* cited by examiner

*Primary Examiner* — Ryan Severson
*Assistant Examiner* — Anh Dang
(74) *Attorney, Agent, or Firm* — Ostrolenk Faber LLP

(57) ABSTRACT

A surgical operating apparatus includes an ultrasonic transducer which generates ultrasonic vibration, a transducer cover including a storing section which stores the ultrasonic transducer, an electric contact portion provided on an outer peripheral surface of a distal end portion of the transducer cover, and an insulative projection portion which is provided at a distal end portion of the transducer cover and projects more radially outward than an outer peripheral surface of the electric contact portion.

6 Claims, 34 Drawing Sheets

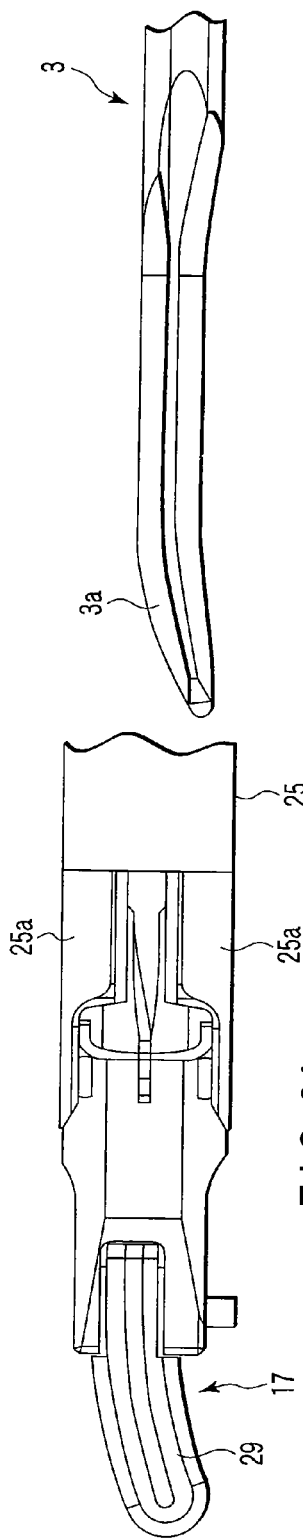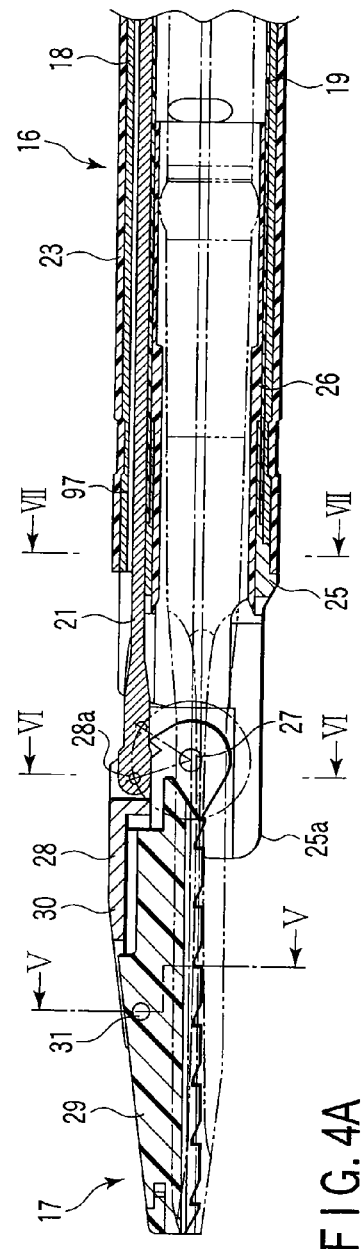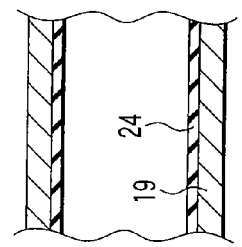

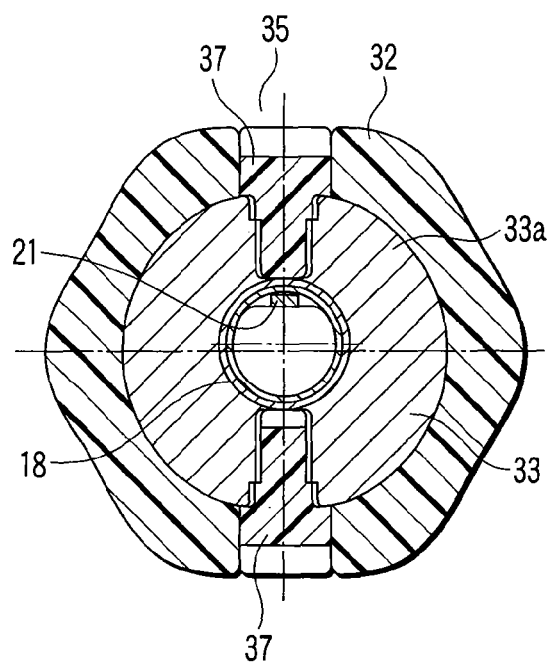
F I G. 9A
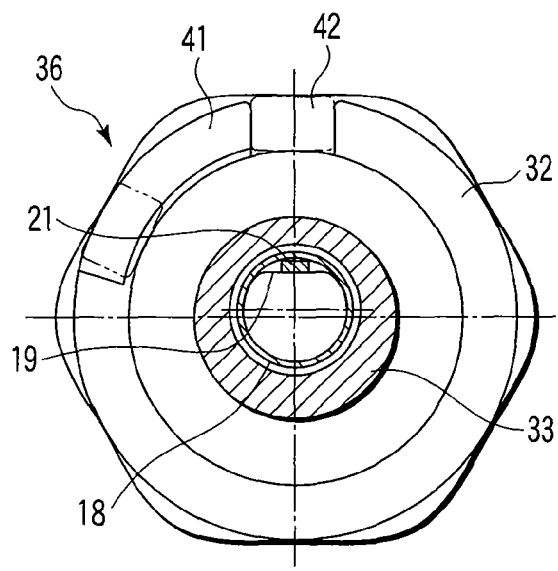
F I G. 9B

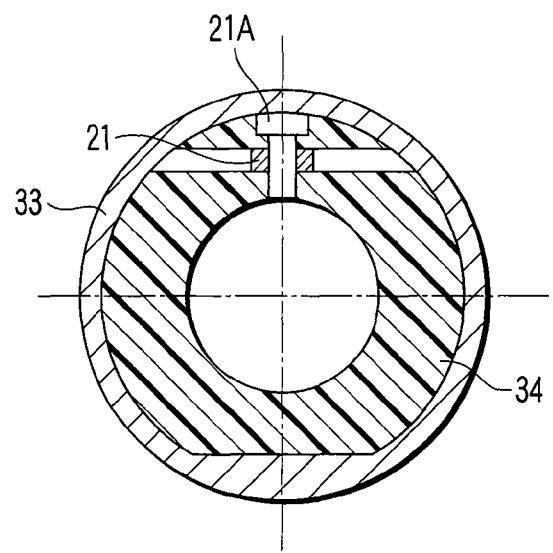
F I G. 10
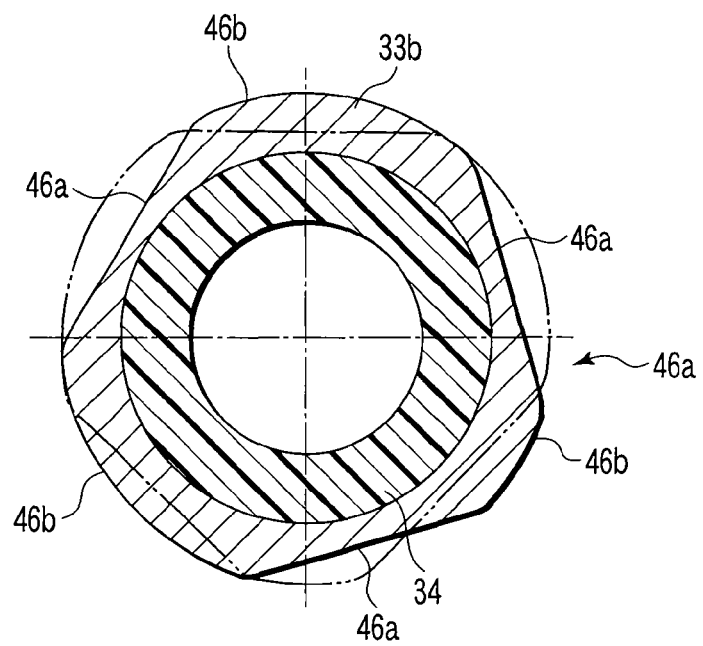
F I G. 11

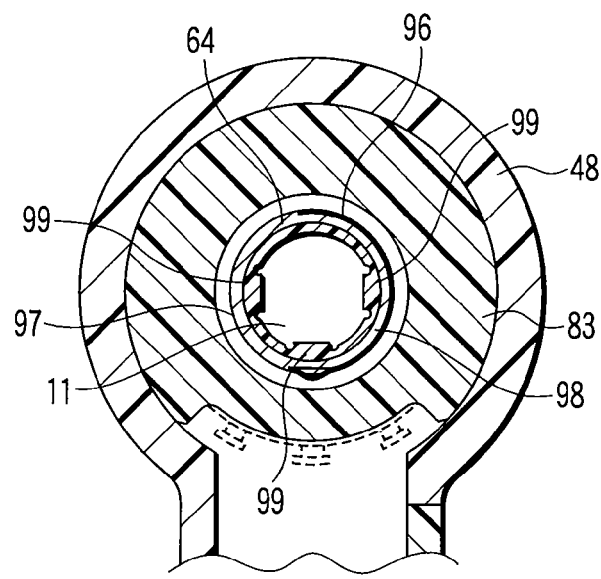
F I G. 19
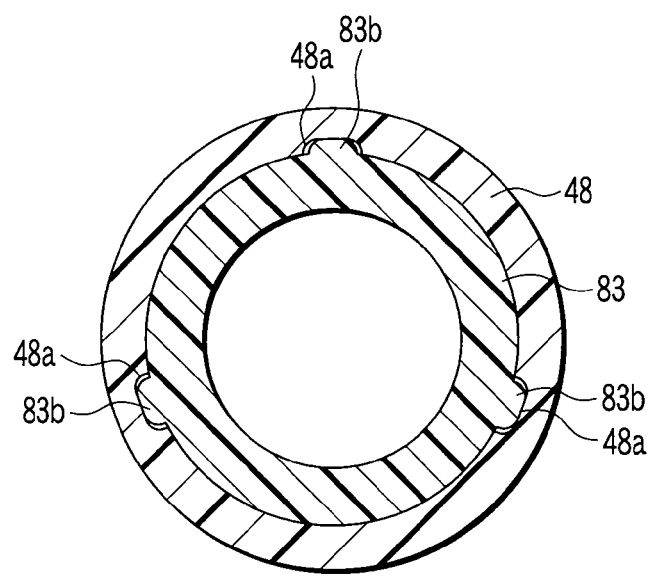
F I G. 20

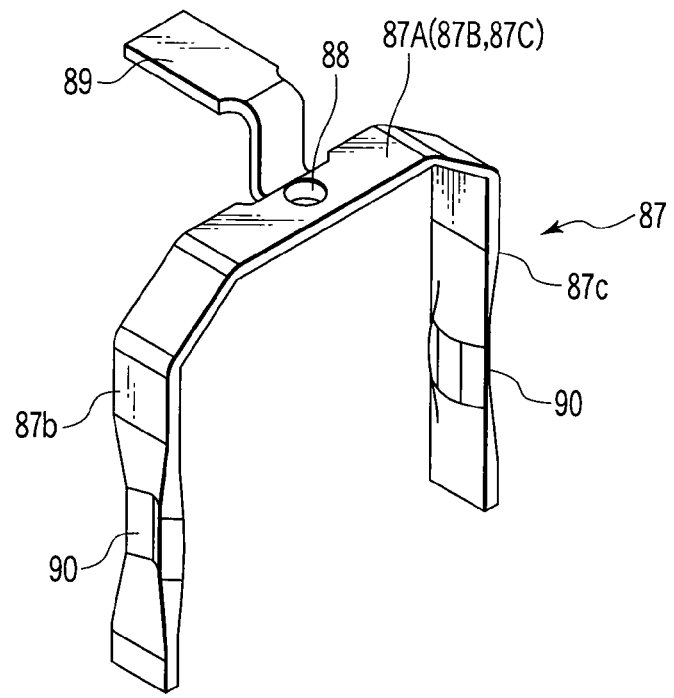
F I G. 27
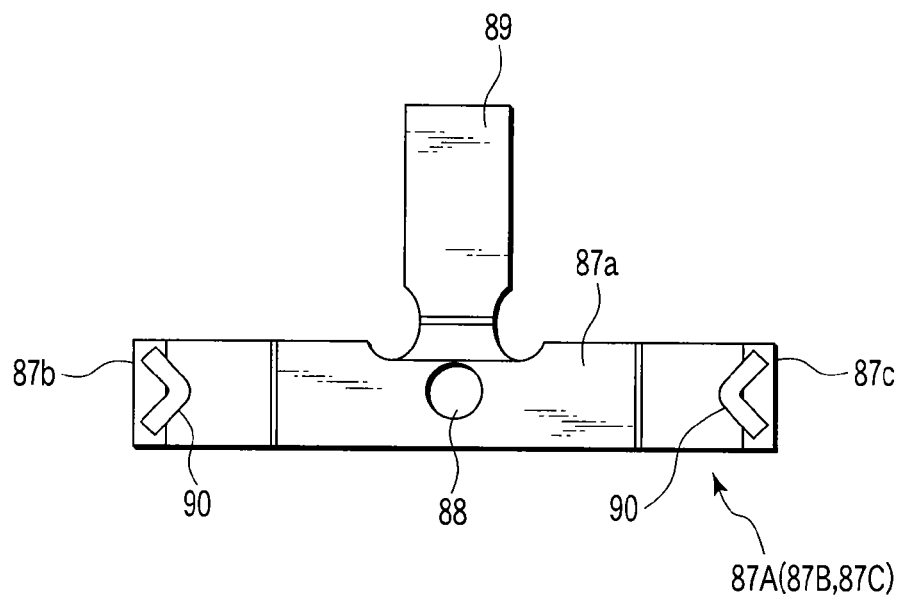
F I G. 28

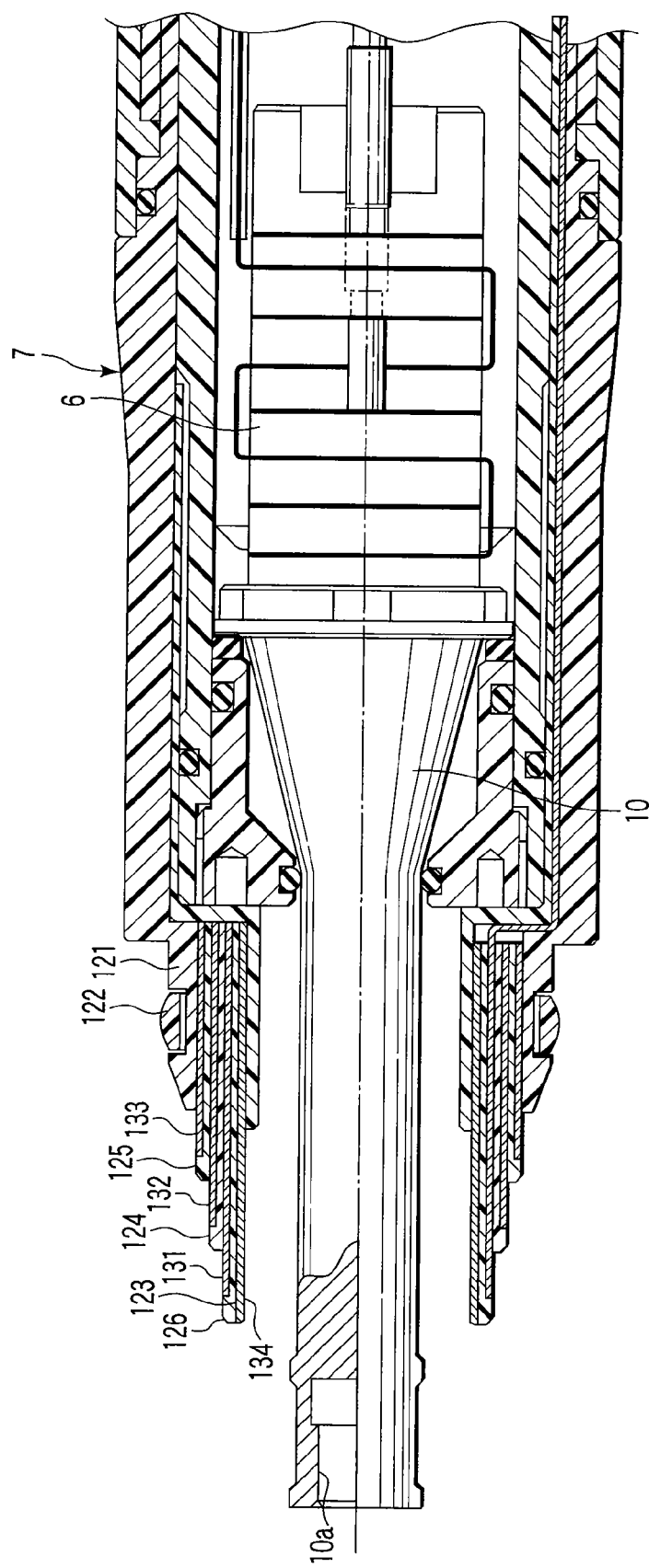
F I G. 36

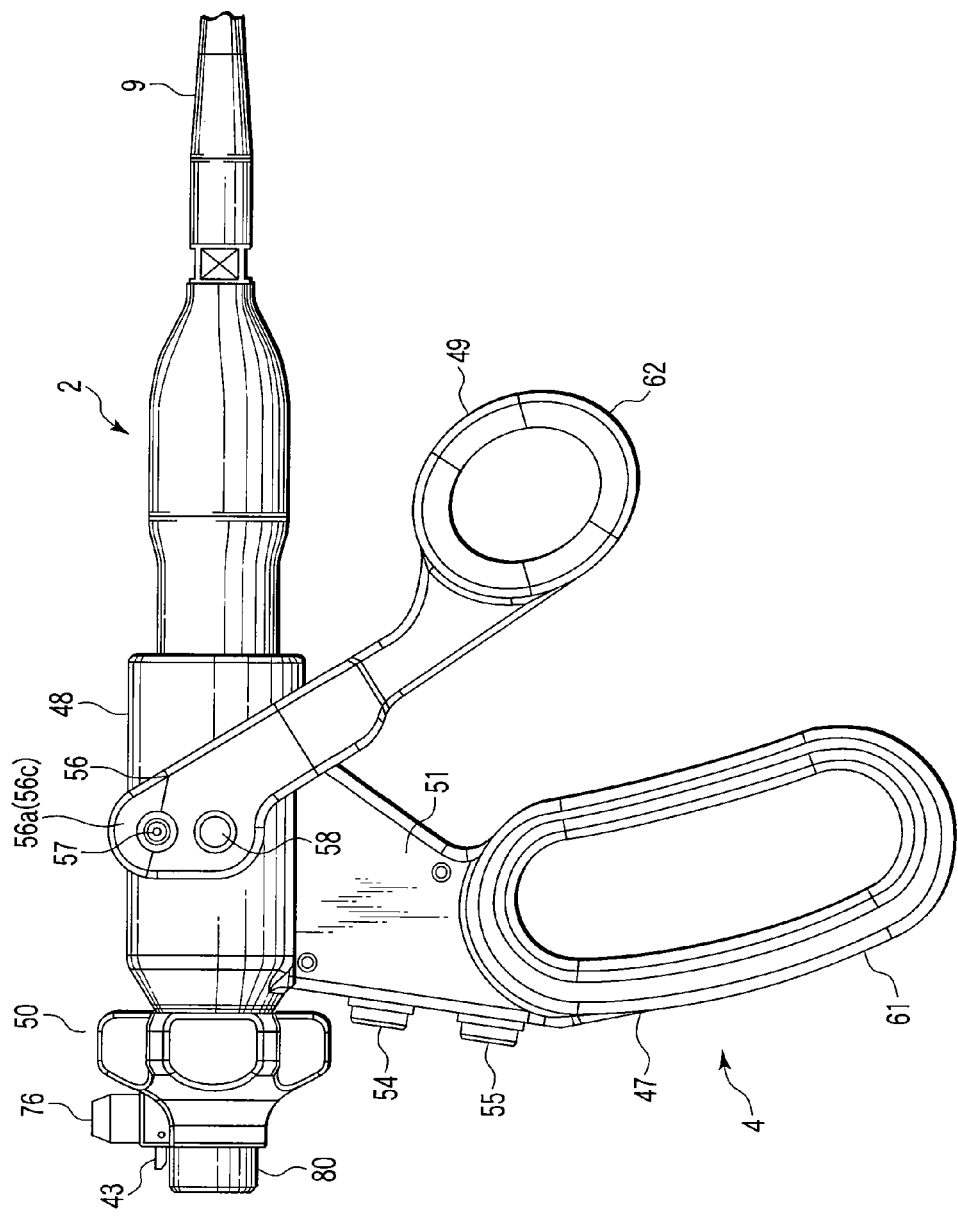
F I G. 37

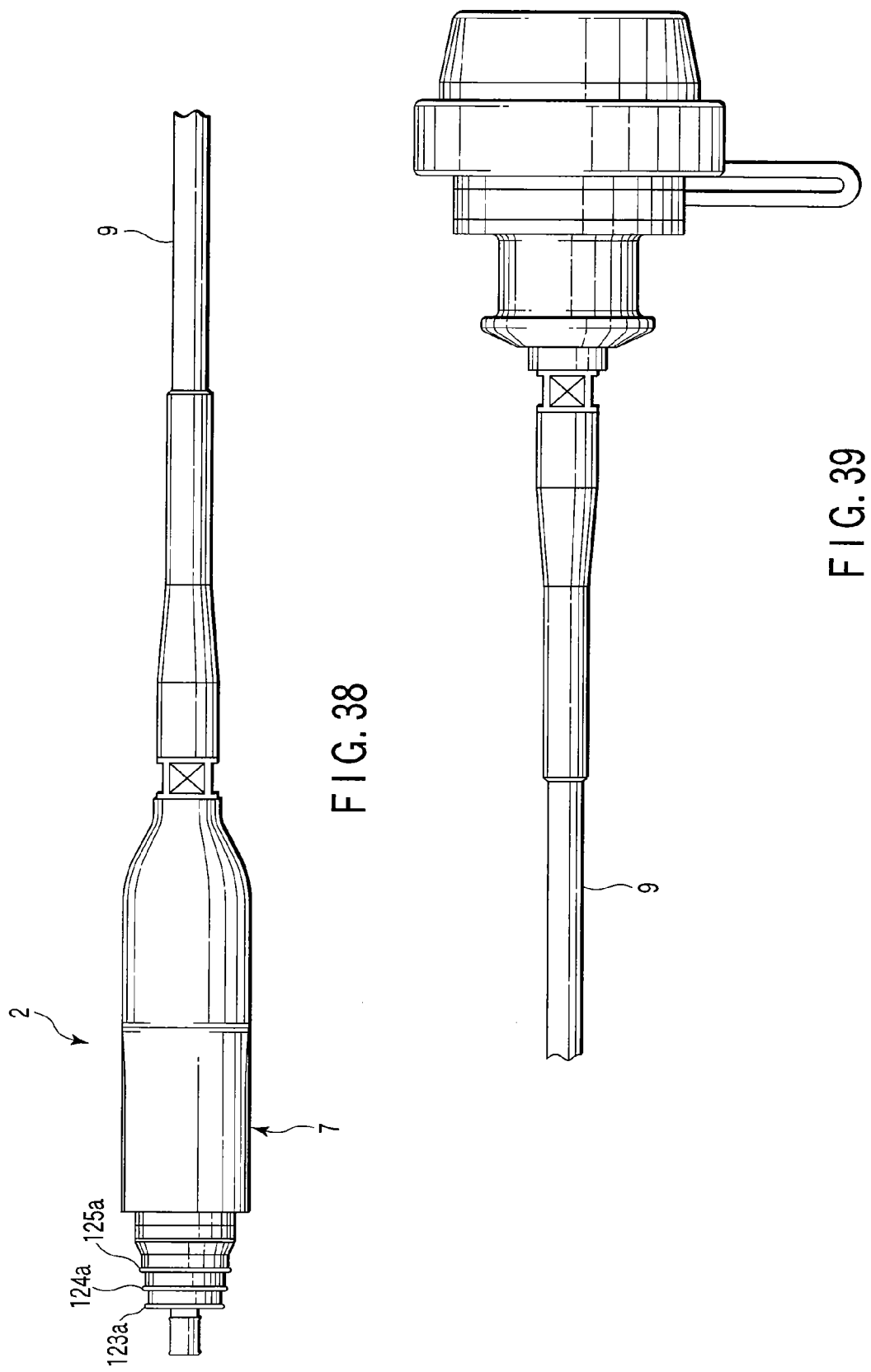

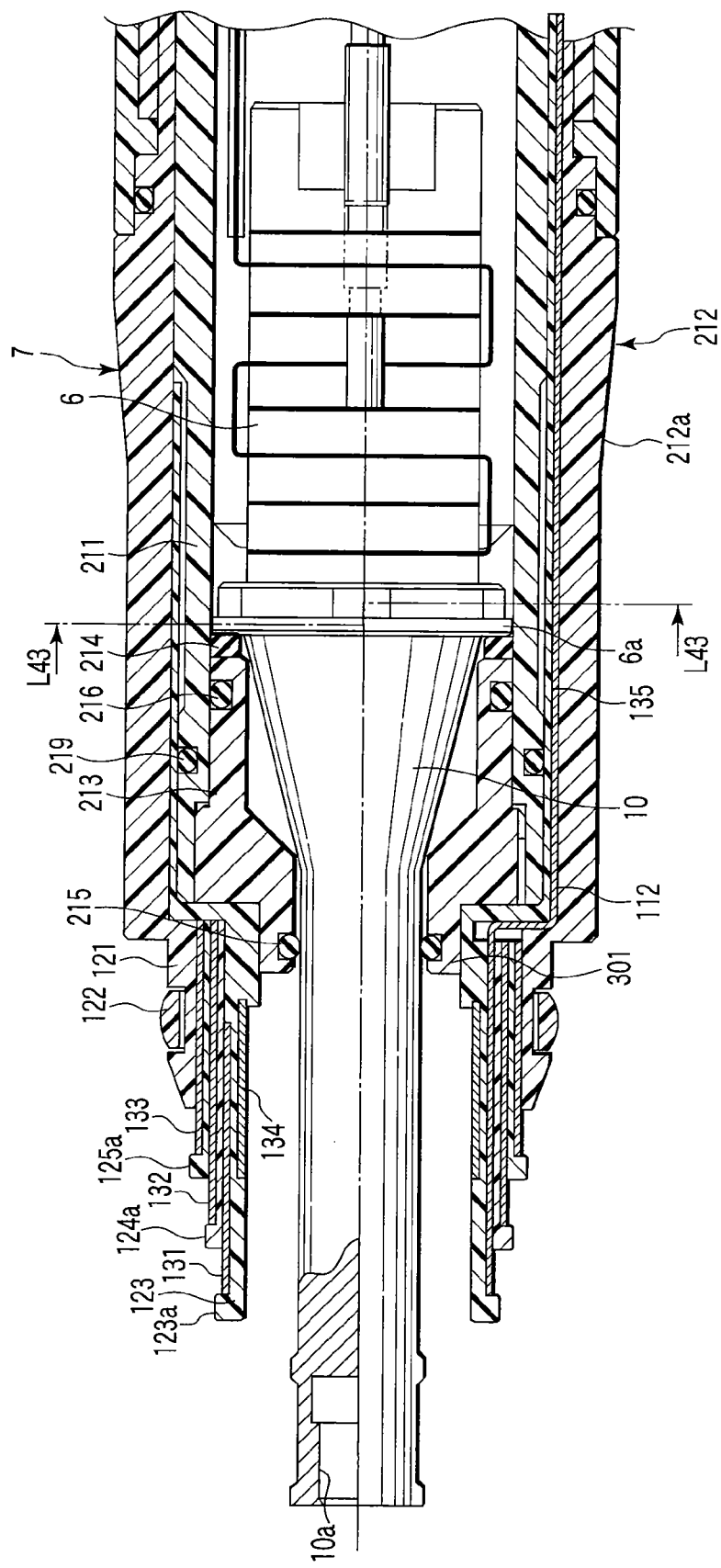
F I G. 41

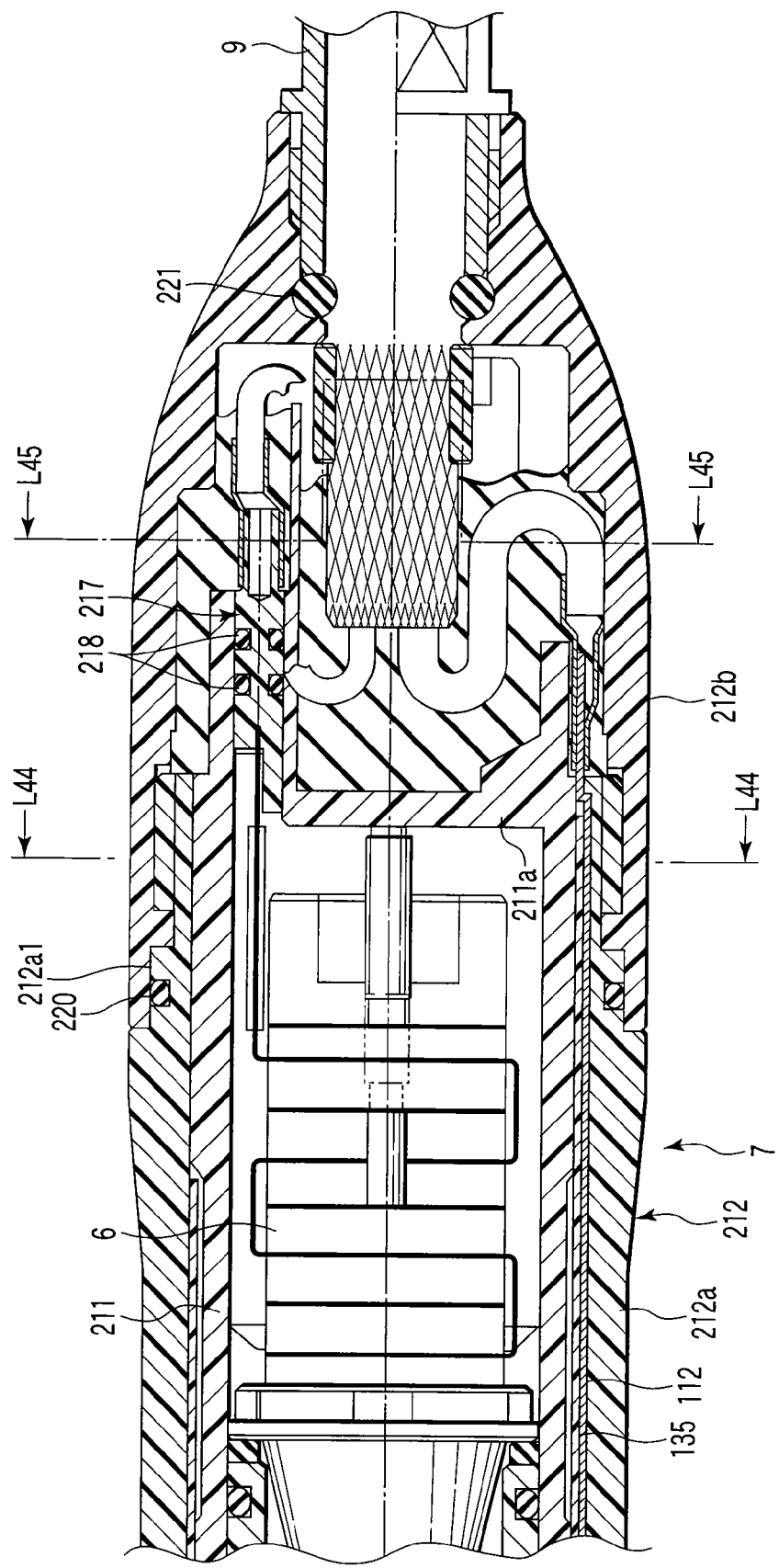
F I G. 42

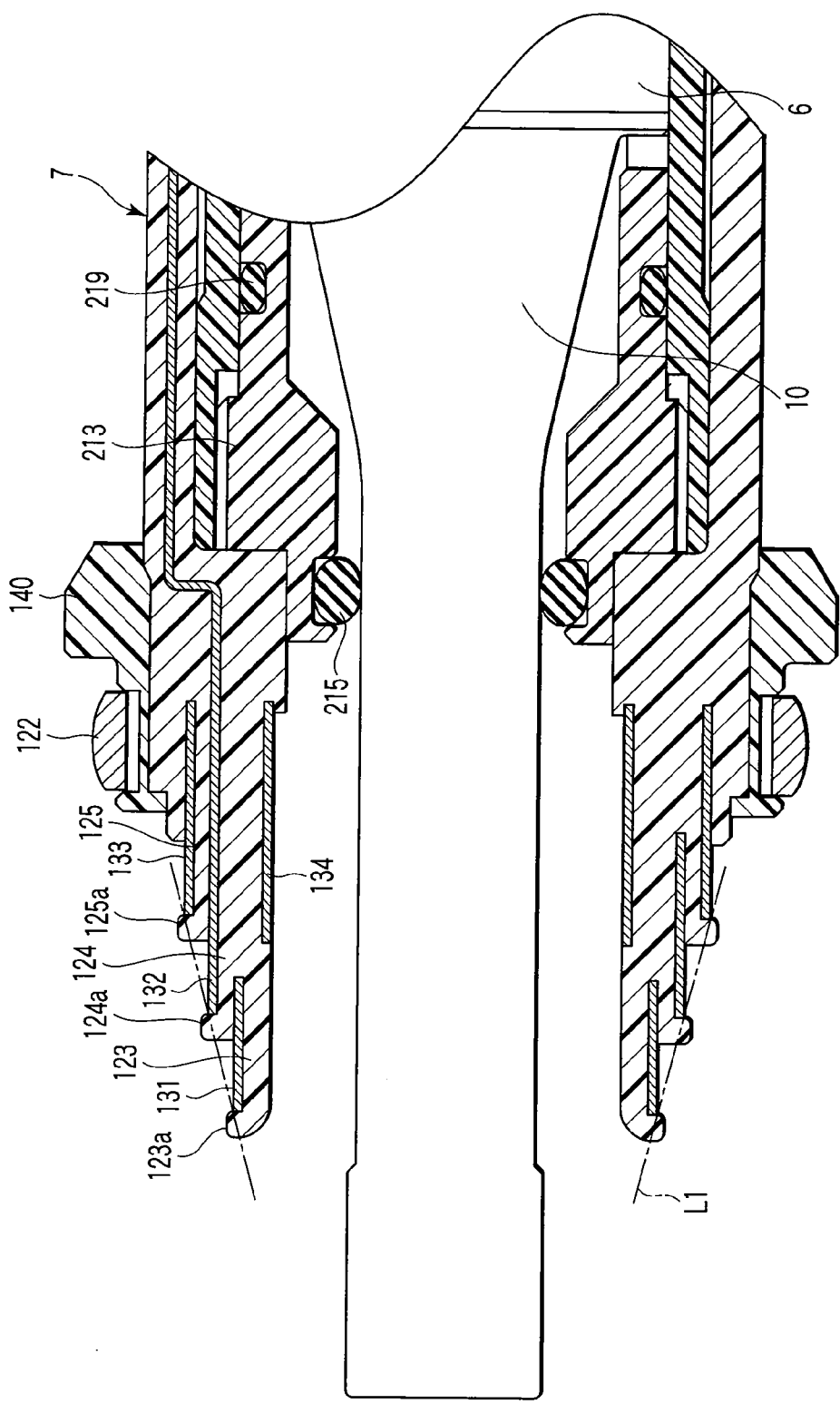
F I G. 49

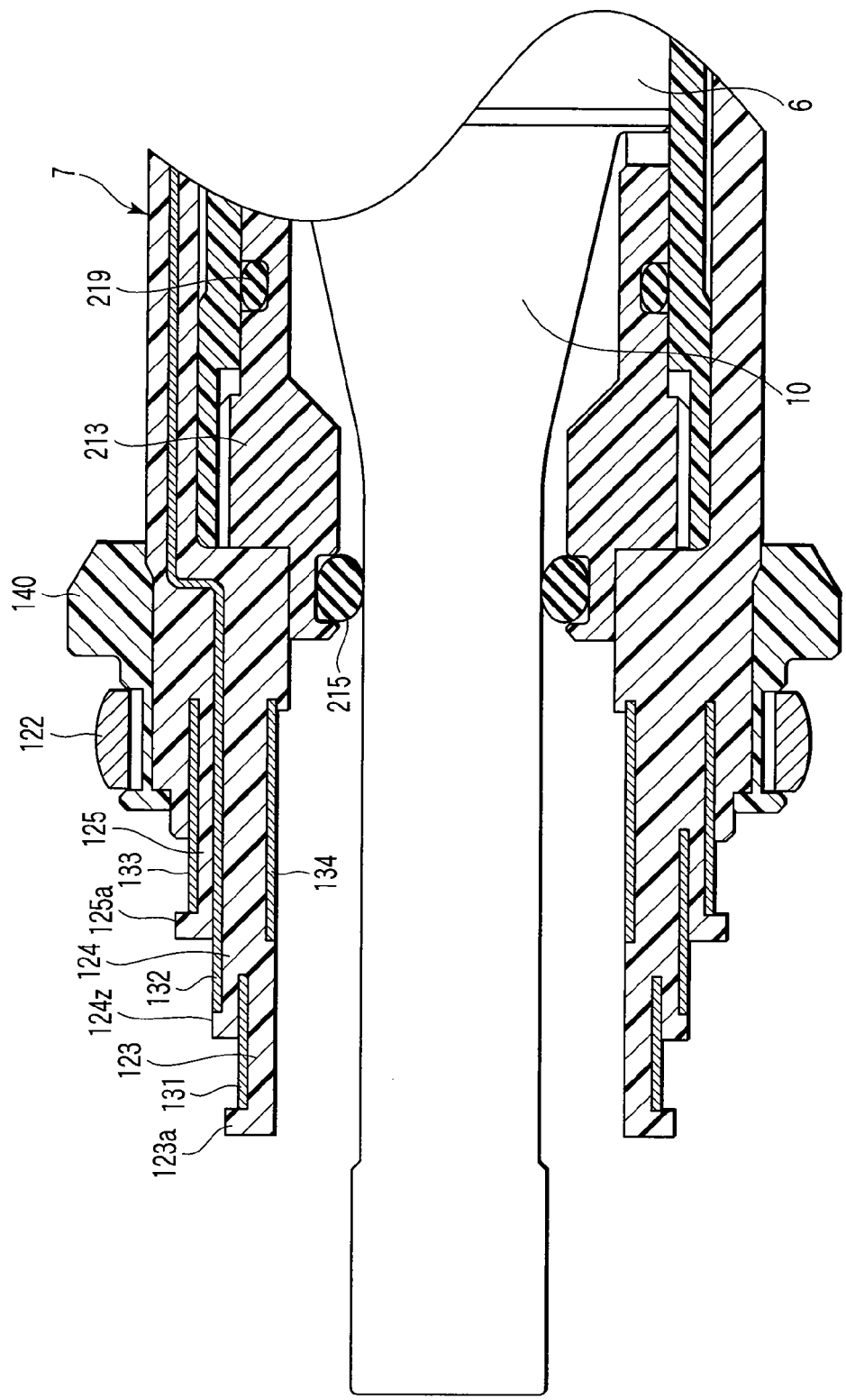
F I G. 50

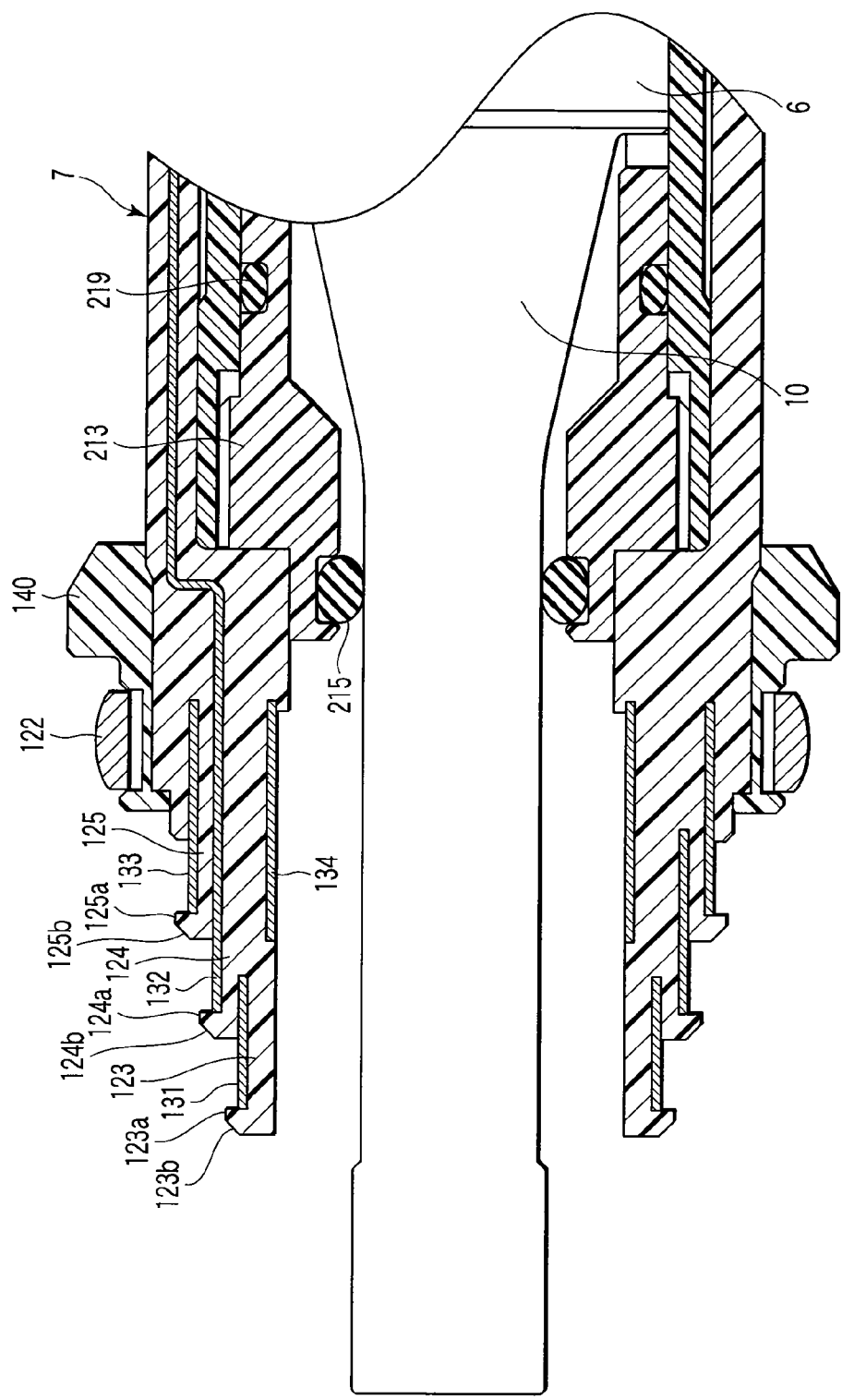
F I G. 51

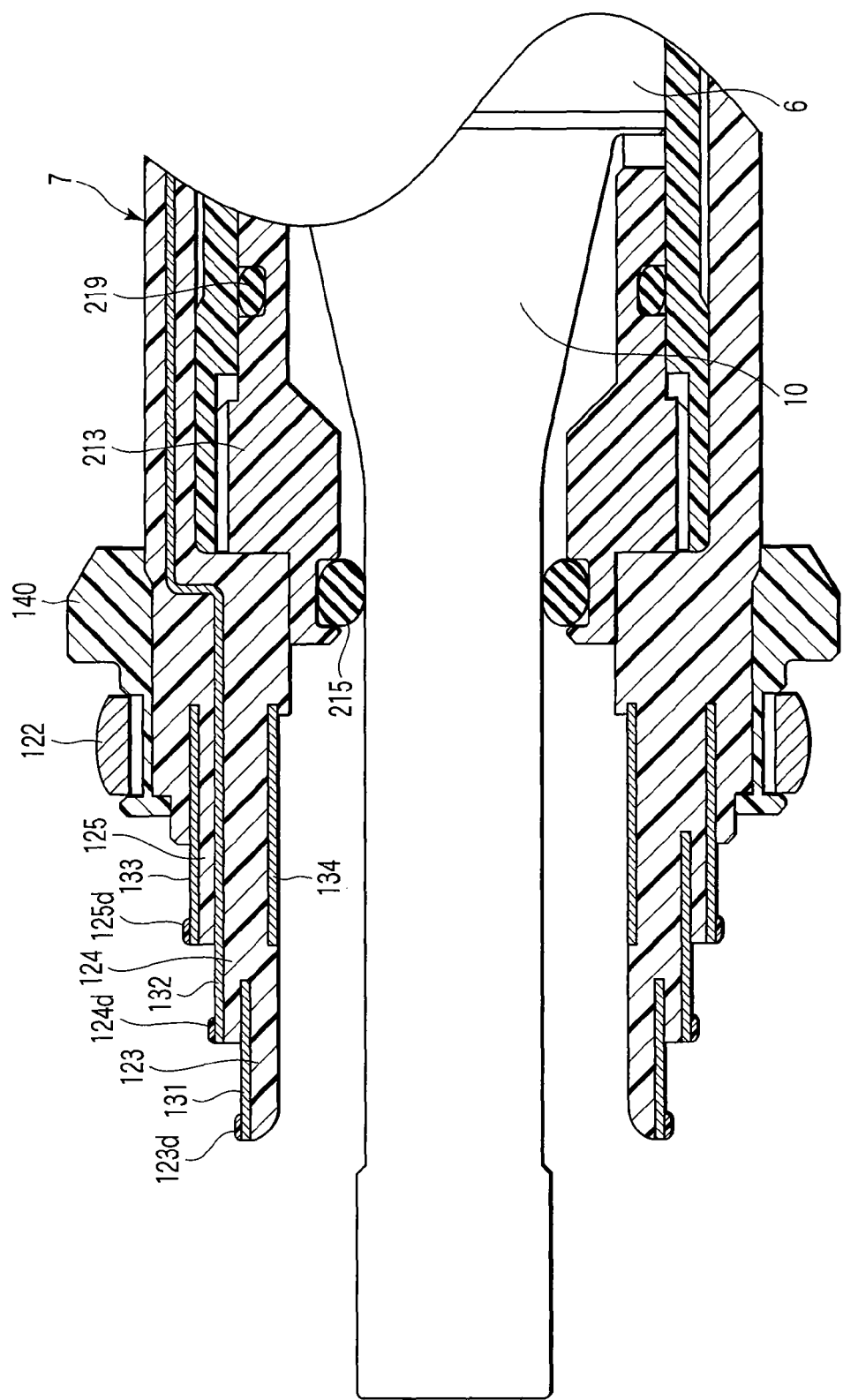
F I G. 53

SURGICAL OPERATING APPARATUS

BACKGROUND OF THE INVENTION

The present invention relates to a surgical operating apparatus which can perform therapeutic treatment, such as incision, resection or coagulation, of a living tissue by making use of composite energy of ultrasonic waves and high-frequency waves, and can also perform therapeutic treatment by high-frequency waves.

Jpn. Pat. Appln. KOKAI Publication No. 2004-154331 (patent document 1) and Jpn. Pat. Appln. KOKAI Publication No. 2003-339731 (patent document 2), for instance, disclose ultrasonic operating apparatuses as general examples of a surgical operating apparatus which can perform therapeutic treatment, such as incision, resection or coagulation, of a living tissue by making use of ultrasonic waves and can also perform therapeutic treatment by high-frequency waves.

Patent document 1 discloses an ultrasonic operating apparatus which is configured such that an ultrasonic probe and a vibration transmission member of a transducer unit are rotatable relative to an operation section. In this case, an operation section body side is provided with electrode pins, and an operation section side coupling member which comes in contact with electrically conductive members of the electrode pins.

The transducer unit is provided with a transducer side coupling member which is rotatably engaged with the operation section side coupling member of the operation section body. A plate spring, which comes in contact with the horn of the transducer unit, is fixed to the transducer side coupling member. A high-frequency electric current, which is supplied to the electrode pins, is transmitted from the operation section side coupling member of the operation section body to the transducer side coupling member of the transducer unit. Subsequently, the high-frequency current is transmitted from the plate spring to the horn, and is further transmitted to an ultrasonic probe at a distal end side via the vibration transmission member. This conduction path of the high-frequency current is shown.

Patent document 2 discloses a structure wherein a connector of a cable is detachably connected to a plug section of an ultrasonic handpiece. The plug section includes a projection which is disposed at the central part, and an annular wall surrounding the periphery of the projection. Electric contacts are provided at positions on the peripheral surface of the projection, which is surrounded by the annular wall. The connector of the cable is provided with contact portions which are electrically connectable to the electric contacts.

BRIEF SUMMARY OF THE INVENTION

According to an aspect of the present invention, there is provided a surgical operating apparatus comprising: an ultrasonic transducer which generates ultrasonic vibration; a transducer cover including a storing section which stores the ultrasonic transducer; an electric contact portion provided on an outer peripheral surface of a distal end portion of the transducer cover; and an insulative projection portion which is provided at a distal end portion of the transducer cover and projects more radially outward than an outer peripheral surface of the electric contact portion.

Preferably, the transducer cover includes a stepwise connection cylindrical portion at a distal end portion thereof, a plurality of said electric contact portions are juxtaposed at the connection cylindrical portion, and the projection portion is provided at a distal end of each of the plurality of electric contact portions.

Preferably, the electric contact portions are juxtaposed in at least three stages, and the projection portions are provided only on the electric contact portion of a lowermost stage and the electric contact portion of an uppermost stage.

Preferably, the projection portion provided with a taper surface that is formed on an outer peripheral surface on a distal end side of the transducer cover.

Preferably, the projection portion includes an insulative stationary ring which is fixed on an outer peripheral surface of a distal end portion of the electric contact portion.

Preferably, the projection portion includes an insulative coating portion which is coated on an outer peripheral surface of a distal end portion of the electric contact portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3A is a plan view showing a distal end portion of a sheath unit of the ultrasonic operating apparatus according to the first embodiment;

FIG. 3B is a plan view showing a distal end portion of a probe unit of the ultrasonic operating apparatus according to the first embodiment;

FIG. 4A is a longitudinal cross-sectional view showing a distal end portion of the sheath unit of the ultrasonic operating apparatus according to the first embodiment;

FIG. 4B is a longitudinal cross-sectional view showing an insulating coating of an inner peripheral surface of an inner cylinder;

FIG. 9A is a cross-sectional view taken along line IXA-IXA in FIG. 8;

FIG. 9B is a cross-sectional view taken along line IXB-IXB in FIG. 8;

FIG. 10 is a cross-sectional view taken along line X-X in FIG. 8;

FIG. 11 is a cross-sectional view taken along line XI-XI in FIG. 8;

FIG. 19 is a cross-sectional view taken along line L19-L19 in FIG. 14;

FIG. 20 is a cross-sectional view taken along line L20-L20 in FIG. 14;

FIG. 27 is a perspective view showing an electrode member of the ultrasonic operating apparatus according to the first embodiment;

FIG. 28 is a transverse cross-sectional view showing the electrode member of the ultrasonic operating apparatus according to the first embodiment;

FIG. 36 is a longitudinal cross-sectional view showing an internal structure of a front end portion of the transducer unit;

FIG. 37 is a side view showing a coupled state between the transducer unit and the handle unit;

FIG. 38 is a plan view showing a coupled state between the transducer unit and a cable of the ultrasonic operating apparatus according to the first embodiment;

FIG. 39 is a plan view showing a proximal end portion of a transducer unit cable of the ultrasonic operating apparatus according to the first embodiment;

FIG. 41 is a cross-sectional view taken along line L41-L41 in FIG. 40;

FIG. 42 is a longitudinal cross-sectional view showing a rear end portion of the transducer unit;

FIG. 49 is a longitudinal cross-sectional view showing a connection circular cylindrical portion of the transducer unit of the ultrasonic operating apparatus according to the first embodiment;

FIG. 50 is a longitudinal cross-sectional view showing a connection circular cylindrical portion of a transducer unit of an ultrasonic operating apparatus according to a second embodiment of the present invention;

FIG. 51 is a longitudinal cross-sectional view showing a connection circular cylindrical portion of a transducer unit of an ultrasonic operating apparatus according to a third embodiment of the present invention;

FIG. 53 is a longitudinal cross-sectional view showing a connection circular cylindrical portion of a transducer unit of an ultrasonic operating apparatus according to a fifth embodiment of the present invention.

DETAILED DESCRIPTION OF THE INVENTION

Figure 1:
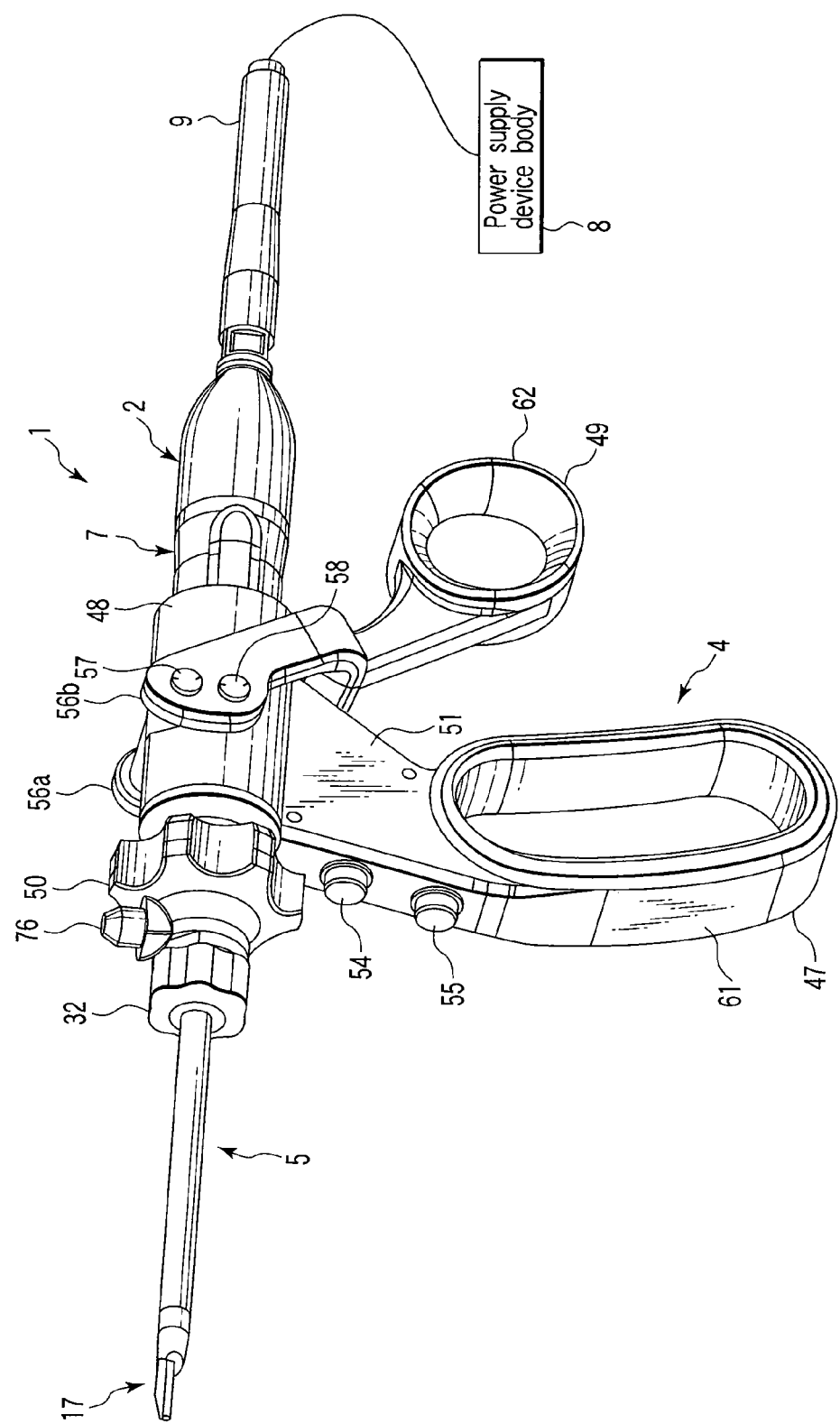
FIG. 1 is a perspective view that schematically shows the entire structure of an ultrasonic operating apparatus which is a surgical operating apparatus according to a first embodiment of the present invention.

FIG. 1 to FIG. 49 show a first embodiment. FIG. 1 schematically shows the entire structure of a handpiece 1 of an ultrasonic operating apparatus according to the present embodiment. The ultrasonic operating apparatus of the present embodiment is an ultrasonic coagulation/incision operating apparatus which can perform therapeutic treatment, such as incision, resection or coagulation, of a living tissue by making use of ultrasonic waves, and can also perform therapeutic treatment by high-frequency waves.

Figure 2:
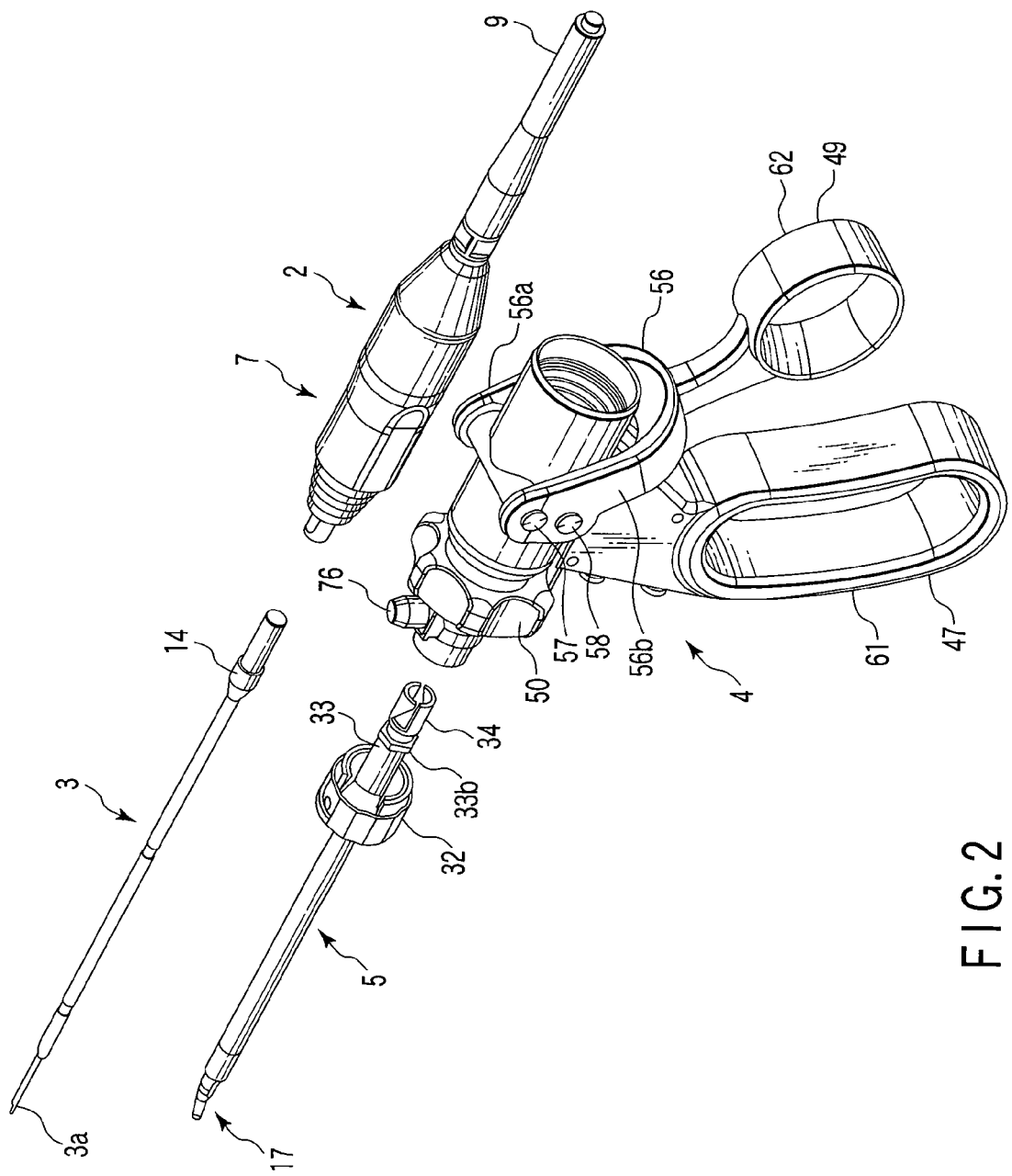
FIG. 2 is a perspective view showing a state in which coupling sections of the ultrasonic operating apparatus according to the first embodiment are disconnected.
Figure 5:
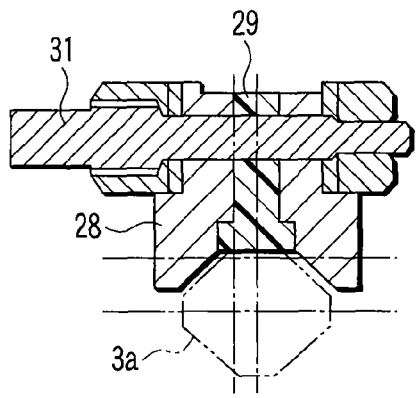
FIG. 5 is a cross-sectional view taken along line V-V in FIG. 4A.

The handpiece 1, as shown in FIG. 2, comprises four units, namely, a transducer unit 2, a probe unit (probe section) 3, a handle unit (handle section) 4 and a sheath unit (sheath section) 5. These four units are detachably coupled.

A transducer 6 (see FIG. 36), which will be described later, is assembled in the transducer unit 2. The transducer 6 generates ultrasonic vibration by a piezoelectric element which converts an electric current to ultrasonic vibration. An outside of the piezoelectric element is covered with a circular cylindrical transducer cover 7. Further, a cable 9 for supplying an electric current for generating ultrasonic vibration from a power supply device body 8 extends from a rear end of the transducer unit 2. A proximal end portion of a horn 10, which increases the amplitude of ultrasonic vibration, is coupled to a front end portion of the ultrasonic transducer 6 within the transducer cover 7. A screw hole portion 10a for attaching the probe is formed at a distal end portion of the horn 10.

Figure 34:
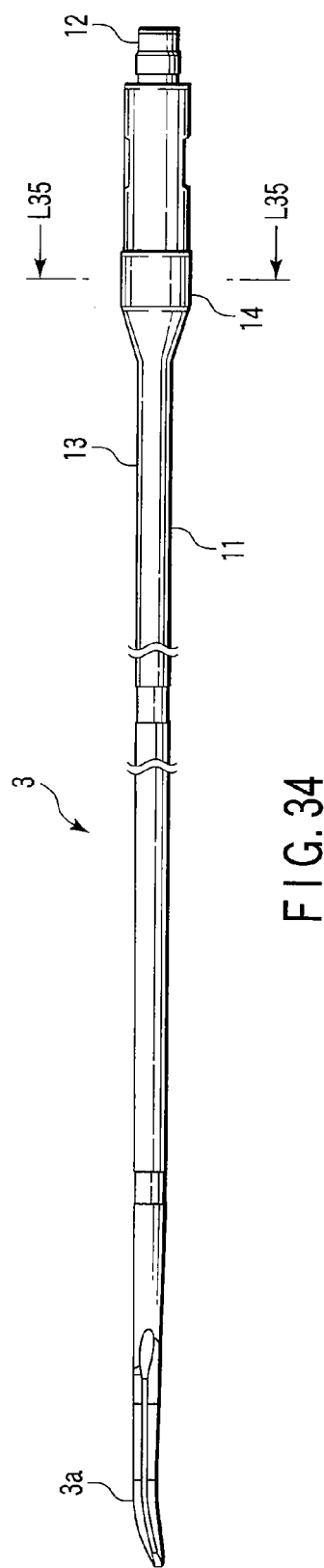
FIG. 34 is a plan view showing a probe unit of the ultrasonic operating apparatus according to the first embodiment.

FIG. 34 shows the external appearance of the entire probe unit 3. The probe unit 3 is designed such that the entire length thereof may become an integer number of times of half-wave length of the ultrasonic vibration. The probe unit 3 includes a metallic rod-shaped vibration transmission member 11. A proximal end portion of the vibration transmission member 11 is provided with a screw portion 12 which is to be engaged with the screw hole portion 10a of the horn 10. The screw portion 12 is engaged with the screw hole portion 10a of the horn 10 of the transducer unit 2. Thereby, the probe unit 3 and the transducer unit 2 are assembled. At this time, a first high-frequency electric path 13, through which a high-frequency current is transmitted, is formed in the coupled body of the ultrasonic transducer 6 and the probe unit 3.

A probe distal end portion 3a, as shown in FIG. 3B, is provided at a distal end portion of the vibration transmission member 11. The probe distal end portion 3a is formed in a substantially J-shaped curved form. The cross-sectional area of the probe unit 3 is decreased in the axial direction at several nodes of vibration in the axial direction, so that an amplitude necessary for therapeutic treatment can be obtained at the probe distal end portion 3a. Rubber rings, which are formed of elastic material in an annular shape, are attached to several positions of nodes of vibration in the axial direction of the probe unit 3. These rubber rings prevent interference between the probe unit 3 and the sheath unit 5.

Figure 35:
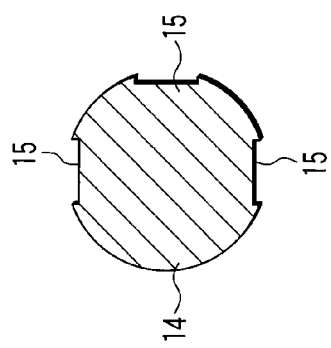
FIG. 35 is a cross-sectional view taken along line L35-L35 in FIG. 34.

A flange portion 14 is provided at the position of the node of vibration on the most proximal end side in the axial direction of the probe unit 3. As shown in FIG. 35, engaging recess portions 15 each having a key groove shape are formed on the outer peripheral surface of the flange portion 14 at three positions in the circumferential direction thereof.

Figure 7:
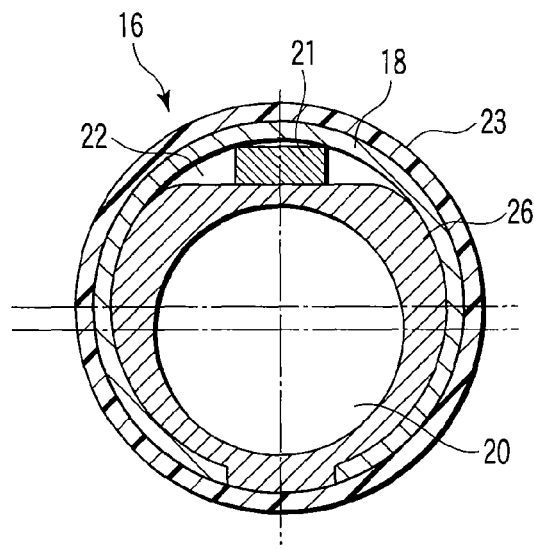
FIG. 7 is a cross-sectional view taken along line VII-VII in FIG. 4A.

The sheath unit 5 includes a sheath body 16, which is formed of a circular cylindrical body, and a jaw 17 which is provided at a distal end of the sheath body 16. The sheath body 16, as shown in FIG. 7, includes a metallic outer cylinder 18 having a circular cross-sectional shape, and a metallic inner cylinder 19 having a non-circular cross-sectional shape, for example, a D-shaped cross section. A channel 22 for passing a driving shaft 21 of the jaw 17 is formed between the outer cylinder 18 and the inner cylinder 19.

As shown in FIG. 4A, the outer peripheral surface of the outer cylinder 18 is covered with an insulation tube 23. As shown in FIG. 4B, the inner peripheral surface of the inner cylinder 19 is covered with an insulation coating 24 of an insulating material. An insulation tube may be provided on the inner peripheral surface of the inner cylinder 19. Electrical insulation from the probe unit 3 is ensured by the insulation coating 24 on the inner cylinder 19. A proximal end portion of a substantially circular cylindrical distal end cover 25 is fixed to a distal end portion of the outer cylinder 18. A pipe-shaped hold member 26, which holds the probe unit 3 so as not to come in contact with the distal end cover 25, is attached to an inner peripheral surface of the proximal end portion of the distal end cover 25. A channel 20 having a circular cross section for passing the probe unit 3 is formed inside the hold member 26.

Figure 6:
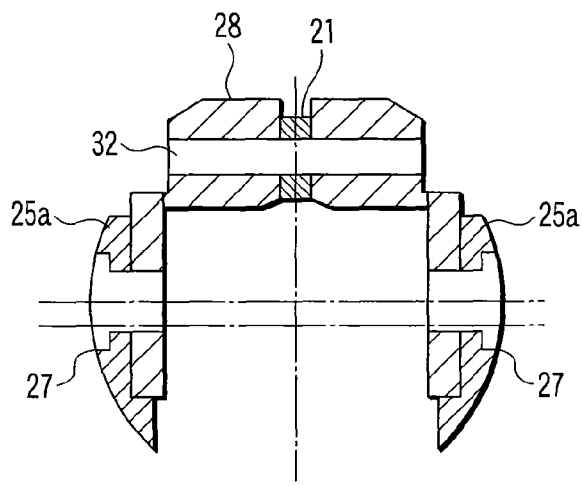
FIG. 6 is a cross-sectional view taken along line VI-VI in FIG. 4A.

As shown in FIG. 3A, a pair of right and left jaw support portions 25a are formed at a distal end portion of the distal end cover 25 so as to extend toward the front side of the outer cylinder 18. As shown in FIG. 6, a metallic jaw body 28 of the jaw 17 is rotatably attached to the jaw support portions 25a via two support pins 27.

The jaw 17, as shown in FIG. 3A, is formed in a substantially J-shaped curved form, which corresponds to the probe distal end portion 3a of the probe unit 3. The jaw 17 is configured to be opposed to the probe distal end 3a of the probe unit 3 and to be rotatable about the two support pins 27 (see FIG. 6). The jaw 17 is rotated and operated between an open position in which the jaw 17 is rotated in a direction away from the probe distal end 3a of the probe unit 3 and a closed position in which the jaw 17 is rotated in a direction toward the probe distal end 3a of the probe unit 3. By the operation of rotating the jaw 17 to its closed position, a living tissue is held between the jaw 17 and the probe distal end 3a of the probe unit 3.

The jaw body 28 includes a hold member 29 which is formed of a resin such as PTFE, and a metallic hold portion attachment member 30 which holds the hold member 29. The hold member 29 is attached to the hold portion attachment member 30 by a pin 31 so as to be rotatable over a predetermined angle (see FIG. 5). Further, as shown in FIG. 4A, a distal end portion of the driving shaft 21 is coupled to the rear end of the jaw body 28 via a pin 28a. The driving shaft 21 extends in the inside of the distal end cover 25, and further extends between the outer cylinder 18 and inner cylinder 19 of the sheath body 16, as shown in FIG. 7, to the proximal end side of the sheath body 16.

Figure 8:
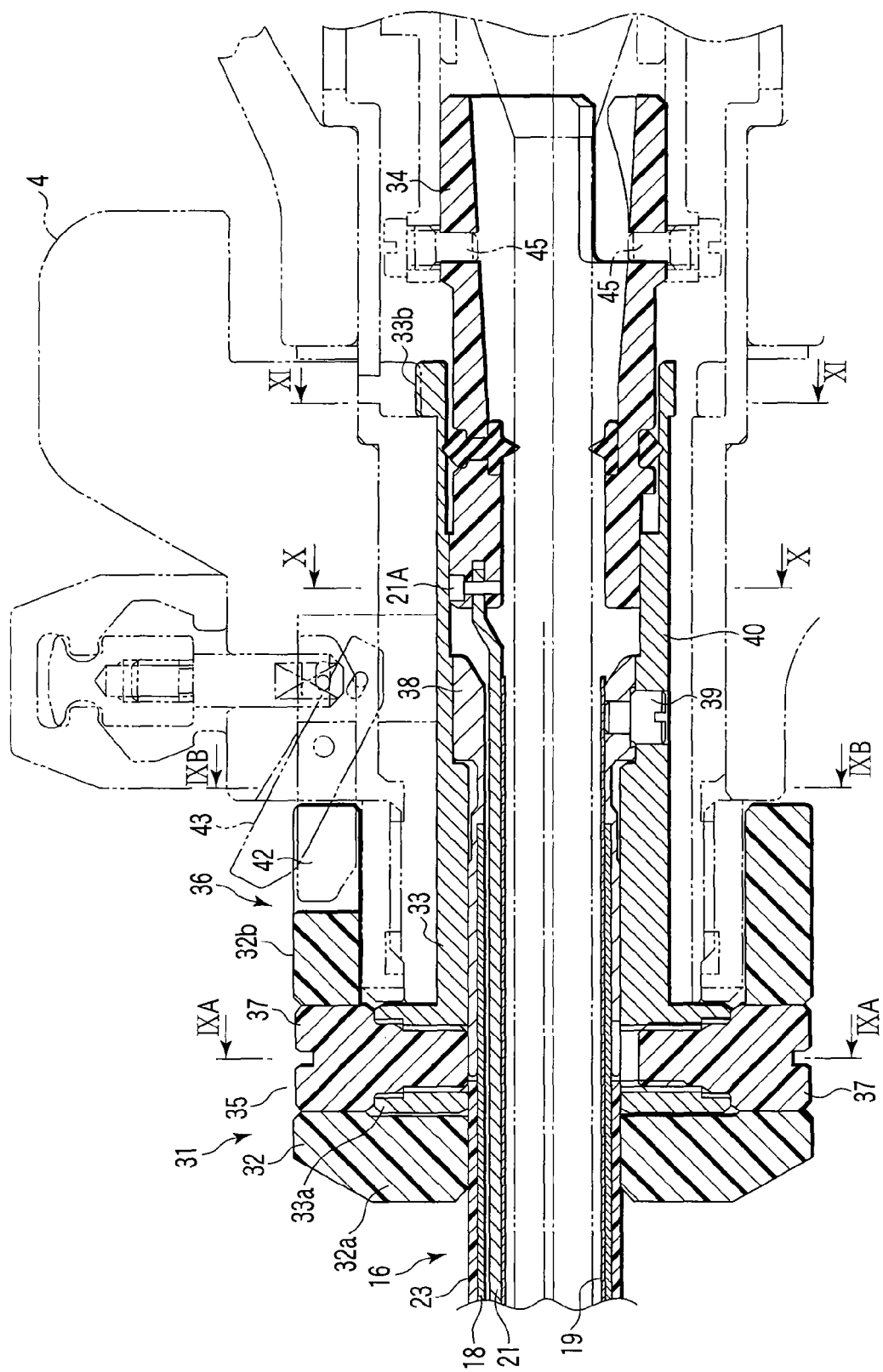
FIG. 8 is a longitudinal cross-sectional view showing a proximal end portion of the sheath unit of the ultrasonic operating apparatus according to the first embodiment.

FIG. 8 shows a proximal end portion of the sheath body 16. The proximal end portion of the sheath body 16 is provided with an attachment/detachment mechanism section 31 for attachment/detachment to/from the handle unit 4. The attachment/detachment mechanism section 31 includes a circular cylindrical large-diameter knob member 32 which is formed of a resin material, a guide cylinder body 33 which is formed of a metallic circular cylinder body, and a circular cylindrical connection tube body 34 which is formed of a resin material.

The knob member 32 includes a ring-shaped first fixing portion 32a which is disposed at a front end part, and a circular cylindrical second fixing portion 32b which is disposed at a rear end part. The inner peripheral surface of the first fixing portion 32a is fixed to the outer peripheral surface of the proximal end portion of the sheath body 16. The second fixing portion 32b of the knob member 32 includes a fixing portion 35 of the guide cylinder body 33 that is disposed on the front end side, and an attachment/detachment portion 36 for attachment/detachment to/from the handle unit 4 that is disposed on the rear end part side.

The guide cylinder body 33 includes a large-diameter front-end flange portion 33a which is disposed at the front end part, and an outer peripheral flange portion 33b which is disposed on the rear end part side. As shown in FIG. 9A, the front-end flange portion 33a of the guide cylinder body 33 is fixed to the knob member 32 by two resin-made fixing screws 37 in the state in which the front-end flange portion 33a is inserted in the knob member 32.

A metallic connection pipe 38 is provided inside the guide cylinder body 33. An inner peripheral surface of a front end portion of the connection pipe 38 is fixed by laser welding to the outer cylinder 18 of the sheath body 16. Further, the connection pipe 38 and guide cylinder body 33 are fixed by a metallic fixing screw 39. Thereby, the guide cylinder body 33, fixing screw 39, connection pipe 38, outer cylinder 18, distal end cover 25, support pins 27 and jaw body 28 are electrically connected, and a sheath-unit-side electric path 40 for transmission of a high-frequency electric current is formed.

Figure 29:
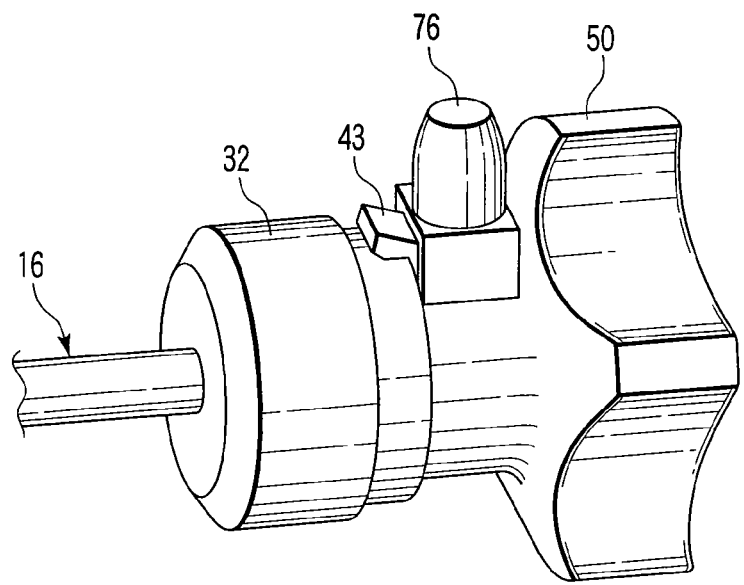
FIG. 29 is a perspective view showing a state before the rotational engagement at the time when the handle unit and sheath unit of the ultrasonic operational apparatus according to the first embodiment are coupled.
Figure 30:
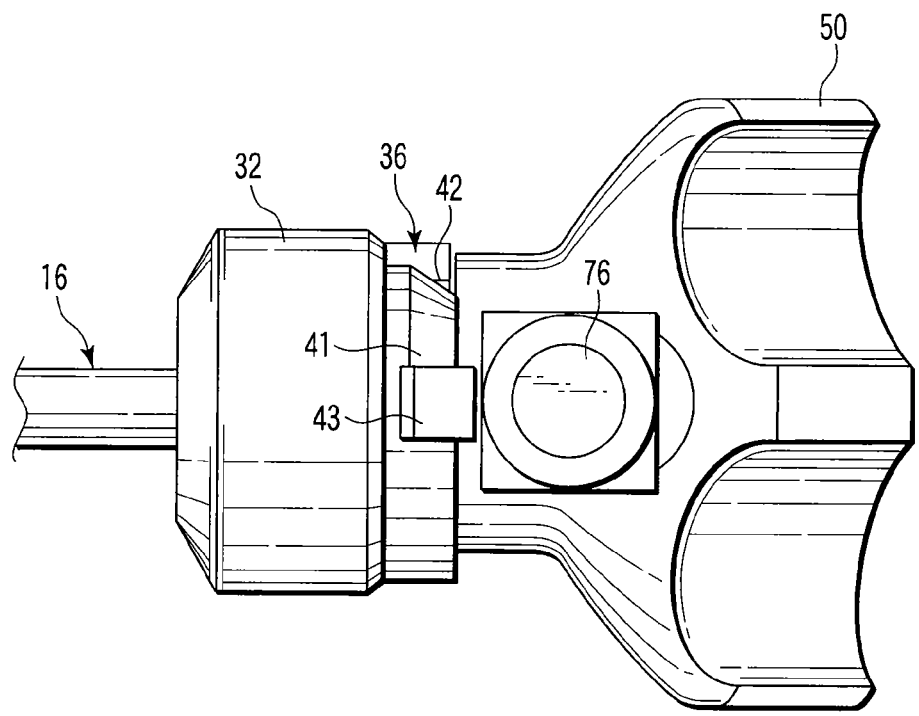
FIG. 30 is a plan view showing a state before the rotational engagement at the time when the handle unit and sheath unit of the ultrasonic operational apparatus according to the first embodiment are coupled.
Figure 31:
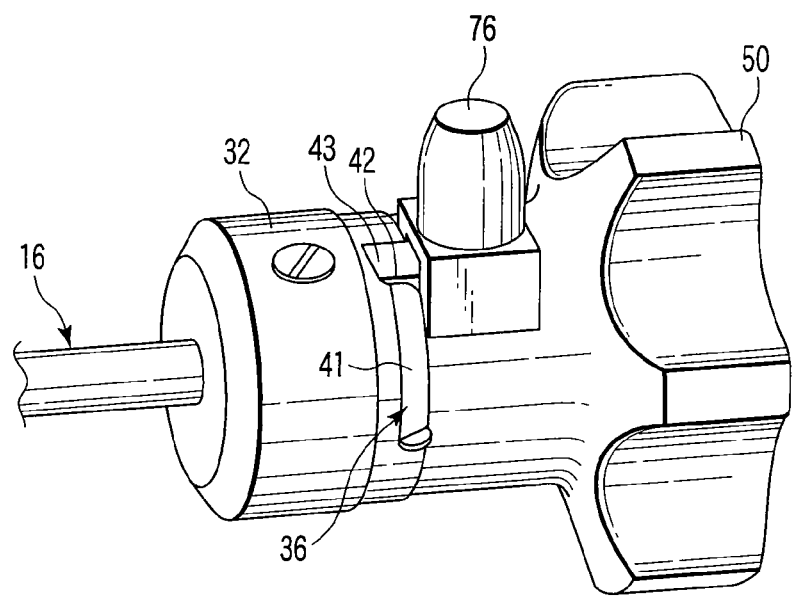
FIG. 31 is a perspective view showing a state after the rotational engagement at the time when the handle unit and sheath unit of the ultrasonic operational apparatus according to the first embodiment are coupled.
Figure 32:
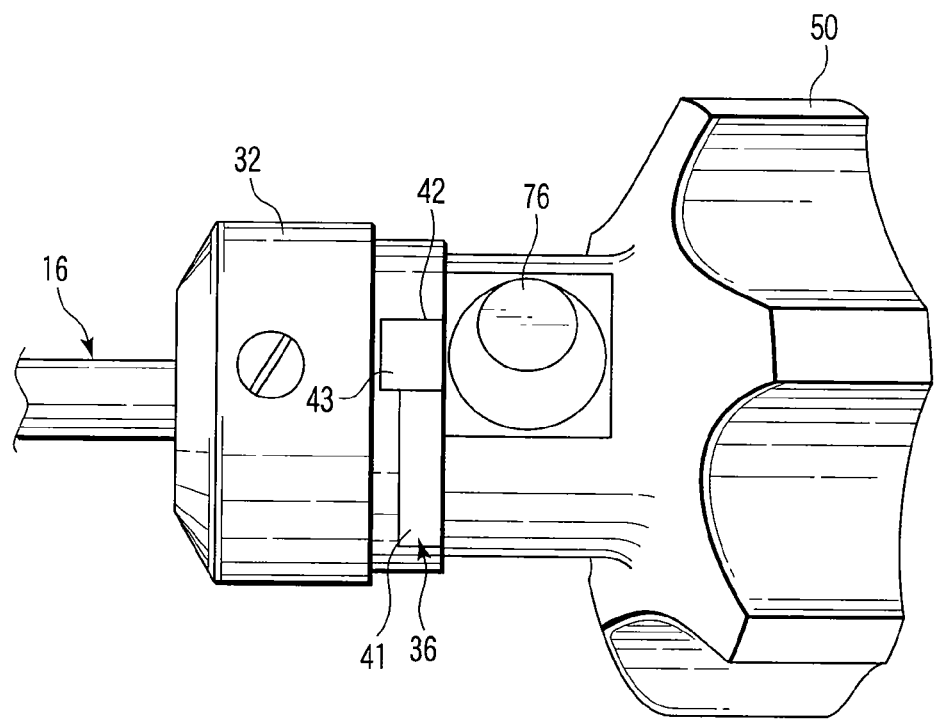
FIG. 32 is a plan view showing a state after the rotational engagement at the time when the handle unit and sheath unit of the ultrasonic operational apparatus according to the first embodiment are coupled.

The attachment/detachment portion 36 of the knob member 32 includes an inclined-surface-shaped guide groove 41 which extends in the circumferential direction, as shown in FIG. 9B, and an engaging recess portion 42 which is formed at one end portion of the guide groove 41. The guide groove 41 has a tapered inclined surface having an outside diameter gradually decreasing toward the rear end portion side of the knob member 32. The engaging recess portion 42 is formed of a recess portion having a smaller diameter than the inclined surface of the guide groove 41. An engaging lever 43 (to be described later) on the handle unit 4 side is disengageably engaged in the engaging recess portion 42. FIG. 31 and FIG. 32 show a state in which the engaging lever 43 is engaged in the engaging recess portion 42, and FIG. 29 and FIG. 30 show a disengagement state in which the engaging lever 43 is disengaged from the engaging recess portion 42.

Figure 12:
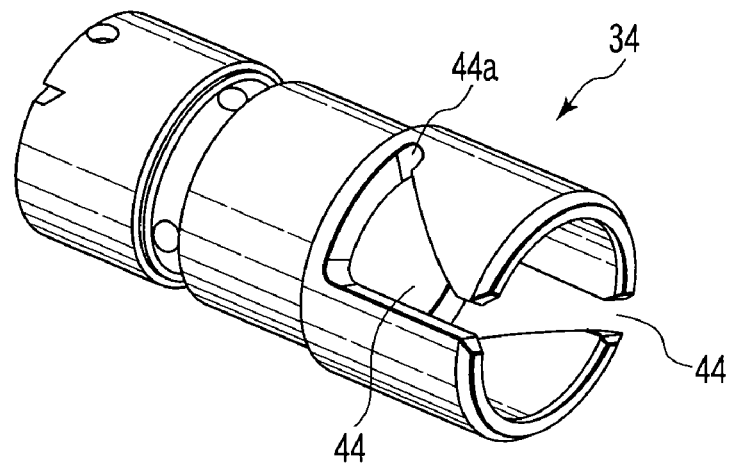
FIG. 12 is a perspective view showing a connection tube body of the sheath unit of the ultrasonic operating apparatus according to the first embodiment.
Figure 13:
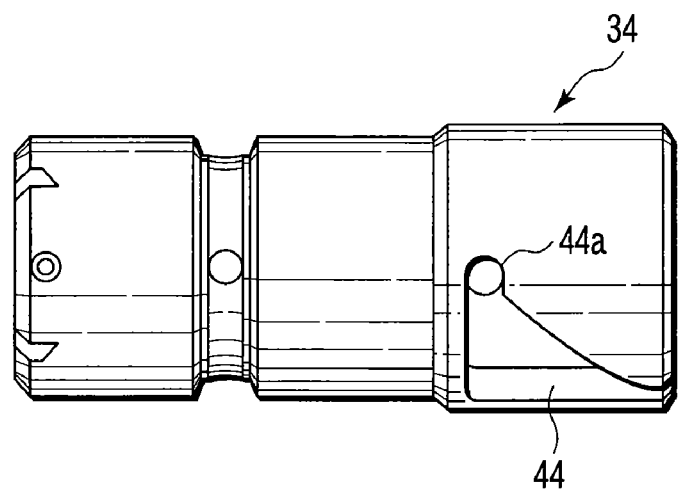
FIG. 13 is a side view showing the connection tube body of the sheath unit of the ultrasonic operating apparatus according to the first embodiment.

The connection tube body 34 is inserted in the guide cylinder body 33 so as to be slidable in the axial direction of the sheath body 16. A proximal end portion of the driving shaft 21 is fixed to a distal end portion of the connection tube body 34 via a pin 21A (see FIG. 10). A proximal end portion of the connection tube body 34 has two guide grooves 44 as shown in FIGS. 12 and 13. The guide grooves 44 are configured such that engaging pins 45 (to be described later) on the handle unit 4 side are disengageably engaged in the guide grooves 44, respectively. An engaging groove 44a, which restricts movement of the engaging pin 45 in the axial direction of the sheath body 16, is formed at a terminal end portion of the guide groove 44.

The outer peripheral flange portion 33b has a non-circular engaging portion 46. The engaging portion 46 has three cutout flat-surface portions 46a at a plurality of locations on the circular outer peripheral surface of the outer peripheral flange portion 33b, for example, at three locations in this embodiment. Corner portions 46b, each having a greater diameter than the flat-surface portion 46a, are formed at connection parts between the three flat-surface portions 46a. Thereby, the engaging portion 46 with a substantially triangular cross section is formed on the outer peripheral flange portion 33b. It is not necessary that the non-circular engaging portion 46 have a substantially triangular shape. The non-circular engaging portion 46 may have any other non-circular shape, for instance, a polygon such as a rectangle or a pentagon.

Figure 14:
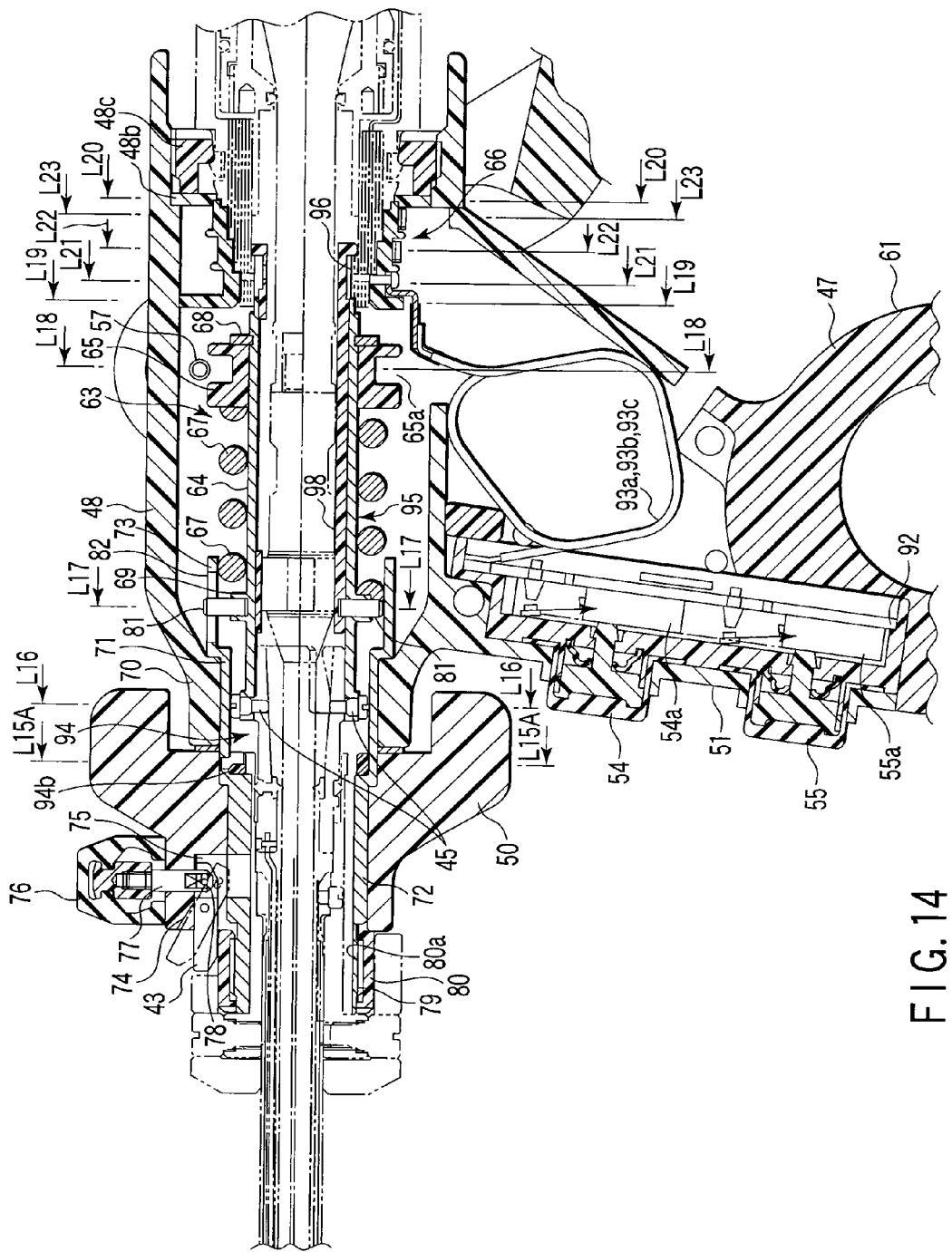
FIG. 14 is a longitudinal cross-sectional view showing an internal structure of a handle unit of the ultrasonic operating apparatus according to the first embodiment.
Figure 33:
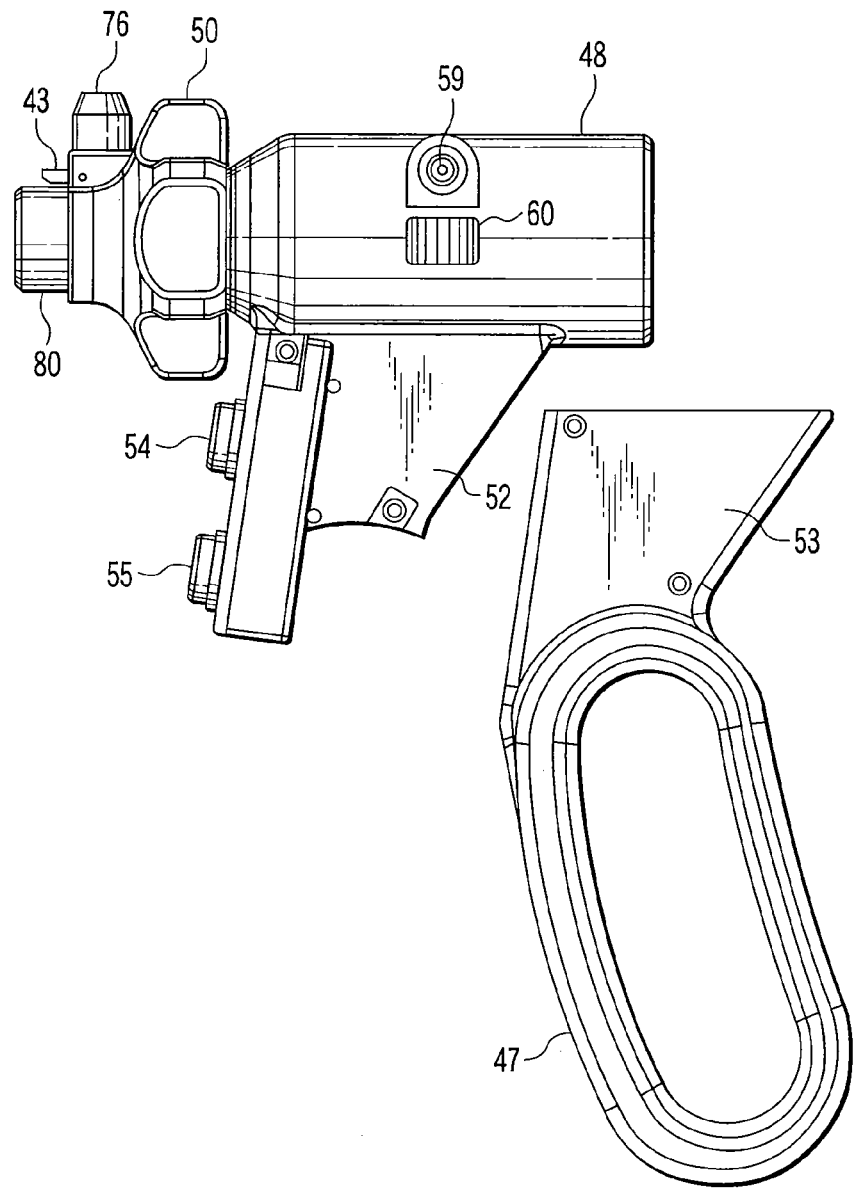
FIG. 33 is a side view showing a state before an attachment member is assembled to a base member of a stationary handle of the handle unit of the ultrasonic operating apparatus according to the first embodiment.

The handle unit 4 mainly includes a stationary handle 47, a hold cylinder 48, a movable handle 49, a rotational operation knob 50 and a handle-unit-side electric path 95 for transmission of a high-frequency electric current (see FIG. 14). The hold cylinder 48 is provided on the upper part of the stationary handle 47. A switch hold section 51 is provided between the stationary handle 47 and the hold cylinder 48. As shown in FIG. 33, the switch hold section 51 includes a switch attachment section 52 which is fixed to a lower end portion of the hold cylinder 48, and a cover member 53 which is fixed to an upper end portion of the stationary handle 47. The switch attachment section 52 has a plurality of hand switch buttons, for example, two hand switch buttons in this embodiment (e.g. a switch button 54 for incision and a switch button 55 for coagulation), which are push-button switches. As shown in FIG. 14, a switch 54a for incision, which is operated by the switch button 54 for incision, a switch 55a for coagulation, which is operated by the switch button 55 for coagulation, and a wiring circuit board 92 are assembled in the switch attachment section 52. A wiring line 93a for incision, which has one end connected to the switch 54a for incision, a wiring line 93b for coagulation, which has one end connected to the switch 55a for coagulation, and a ground wiring line 93c, which has one end connected to a common terminal for grounding, are connected to the wiring circuit board 92. These three wiring lines 93a to 93c are looped and assembled in the switch hold section 51.

Figure 18:
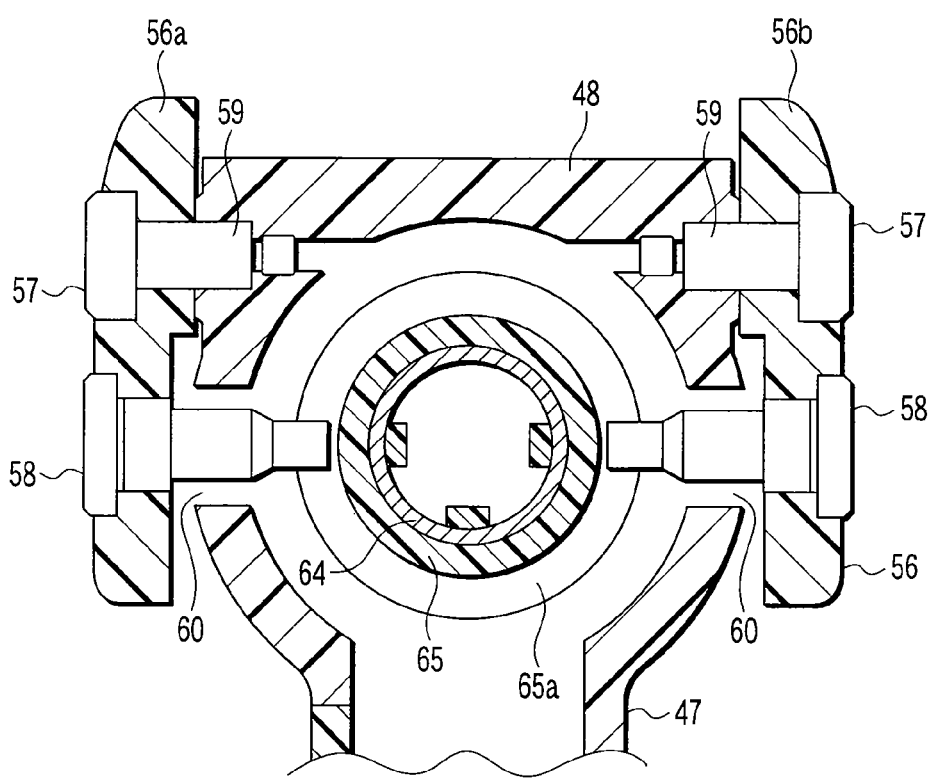
FIG. 18 is a cross-sectional view taken along line L18-L18 in FIG. 14.

The movable handle 49 has a substantially U-shaped arm section 56 at an upper part thereof. The U-shaped arm section 56 includes two arms 56a and 56b, as shown in FIG. 18. The movable handle 49 is assembled to the hold cylinder 48 in the state in which the hold cylinder 48 is inserted between the two arms 56a and 56b.

Each of the arms 56a and 56b has a support pin 57 and an operation pin 58. A pin receiving hole portion 59 and a window portion 60 are formed in each of both side portions of the hold cylinder 48. The support pin 57 of each arm 56a, 56b is inserted in the pin receiving hole portion 59 of the hold cylinder 48. Thereby, an upper end portion of the movable handle 49 is rotatably supported on the hold cylinder 48 via the support pins 57.

Finger hook portions 61 and 62 are provided on lower end portions of the stationary handle 47 and movable handle 49, respectively. By hooking the fingers on the finger hook portions 61 and 62 and holding them, the movable handle 49 rotates via the support pins 57 and the movable handle 49 is opened/closed relative to the stationary handle 47.

The operation pins 58 of the movable handle 49 extend into the hold cylinder 48 through the window portions 60 of the hold cylinder 48. An operation force transmission mechanism 63, which transmits an operation force of the movable handle 49 to the driving shaft 21 of the jaw 17, is provided inside the hold cylinder 48. As shown in FIG. 14, the operation force transmission mechanism 63 mainly comprises a metallic circular cylindrical spring receiving member 64 and a resin-made slider member 65. The spring receiving member 64 is disposed coaxially with the center axis of the hold cylinder 48, and extends in the same direction as the direction of insertion of the probe unit 3.

A proximal end portion of the spring receiving member 64 is coupled to a circular cylindrical contact-point unit 66 (to be described later), which is fixed to a proximal end portion of the hold cylinder 48, so as to be rotatably about the axis and to be advancible/retreatable in the same direction as the direction of insertion of the probe unit 3. The above-described pair of engaging pins 45 on the handle unit 4 side are inwardly projectingly provided at a distal end portion of the spring receiving member 64. When the handle unit 4 and sheath unit 5 are coupled, the pair of engaging pins 45 on the handle unit 4 side are disengageably engaged with the engaging grooves 44a at the terminal end portion of the guide grooves 44 of the sheath unit 5.

A coil spring 67, the slider member 65, a stopper 68 and a spring receiver 69 are provided on an outer peripheral surface of the spring receiving member 64. A front end portion of the coil spring 67 is fixed to the spring receiver 69. The stopper 68 restricts the position of movement of a rear end side of the slider member 65. The coil spring 67 is disposed between the spring receiver 69 and the slider member 65 with a definite amount of mounting force.

An annular engaging groove 65a is formed in a circumferential direction in an outer peripheral surface of the slider member 65. As shown in FIG. 18, the operation pins 58 of the movable handle 49 are inserted and engaged in the engaging groove 65a. If the movable handle 49 is held and the movable handle 49 is closed relative to the stationary handle 47, the operation pins 58 rotate about the support pins 57 in accordance with the rotational operation of the movable handle 49 at this time. The slider member 65, which is in interlock with the rotation of the support pins 57, moves forward along the axial direction. At this time, the spring receiving member 64, which is coupled to the slider member 65 via the coil spring 67, moves forward/backward together with the slider member 65. Thereby, the operation force of the movable handle 49 is transmitted to the connection tube body 34 via the pair of engaging pins 45, and the driving shaft 21 of the jaw 17 moves forward. Thus, the jaw body 20 of the jaw 17 rotates via the support pin 21.

Further, when a living tissue is clamped between the hold member 29 of the jaw 17 and the probe distal end portion 3a of the probe unit 3 by this operation, the hold member 29 rotates over a certain angle about the pin 31 in accordance with the bending of the probe distal end portion 3a so that force uniformly acts over the entire length of the hold member 29. In this state, ultrasonic is output and a living tissue, such as a blood vessel, can be coagulated or cut.

An annular bearing portion 70 is formed at a front end portion of the hold cylinder 48. The bearing portion 70 is metallic, and a circular cylindrical rotation transmission member 71 is coupled to the bearing portion 70 so as to be rotatable about the axis. The rotation transmission member 71 includes a projecting portion 72 which projects forward of the bearing portion 70, and a large-diameter portion 73 which extends to the inner side of the hold cylinder 48 from the bearing portion 70.

The rotational operation knob 50 is fitted and fixed on the projecting portion 72. The engaging lever 43 is provided at the front end portion of the rotational operation knob 50. An intermediate portion of the engaging lever 43 is rotatably coupled to the projecting portion 72 via a pin 74. A proximal end portion of the engaging lever 43 extends to the inside of a lever receiving recess portion 75 which is formed in a front surface of the rotational operation knob 50. An operation button 76 for operating the engaging lever 43 in such a direction as to disengage the engaging lever 43 is provided on an outer peripheral surface of the front end portion of the rotational operation knob 50. An operation pin 77, which is disposed downward, is provided so as to project from the operation button 76. The operation pin 77 extends to the inside of the lever receiving recess portion 75 through a wall hole of the rotational operation knob 50. A proximal end portion of the engaging lever 43 is rotatably coupled to a lower end portion of the operation pin 77 via a pin 78.

A removal prevention ring 80 for the rotational operation knob 50 is provided on a distal end portion of the projecting portion 72. A male threaded portion 79 is formed on the distal end portion of the projecting portion 72. A female threaded portion 80a, which is to be meshed with the male threaded portion 79, is formed on an inner peripheral surface of the removal prevention ring 80. The female threaded portion 80a of the removal prevention ring 80 is meshed and engaged with the male threaded portion 79 of the projecting portion 72, and thereby the rotational operation knob 50 is fixed to the rotation transmission member 71.

Figure 17:
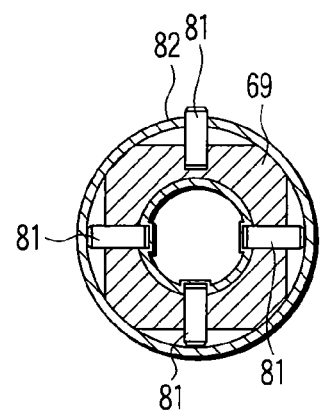
FIG. 17 is a cross-sectional view taken along line L17-L17 in FIG. 14.

As shown in FIG. 17, the spring receiver 69 of the spring receiving member 64 is provided with four metallic positioning pins 81 which project radially outward. An elongated engaging hole portion 82, in which one pin 81 of the spring receiving member 64 is inserted, is formed in the large-diameter portion 73 of the rotation transmission member 71. The engaging hole portion 82 extends in the same direction as the direction of insertion of the probe unit 3. Thereby, when the movable handle 49 is operated, the pin 81 is moved along the engaging hole portion 82 and thus the advancing/retreating movement of the spring receiving member 64 is prevented from being transmitted to the rotation transmission member 71.

On the other hand, when the rotational operation knob 50 is rotated, the rotational movement of the rotation transmission member 71, which rotates together with the rotational operation knob 50, is transmitted to the spring receiving member 64 side via the pin 81. Thereby, when the rotational operation knob 50 is rotated, the assembly unit of the rotation transmission member 71, pin 81, spring receiving member 64, slider member 65 and coil spring 67 within the hold cylinder 48 is rotated together with the rotational operation knob 50 as one body about the axis thereof.

Figure 21:
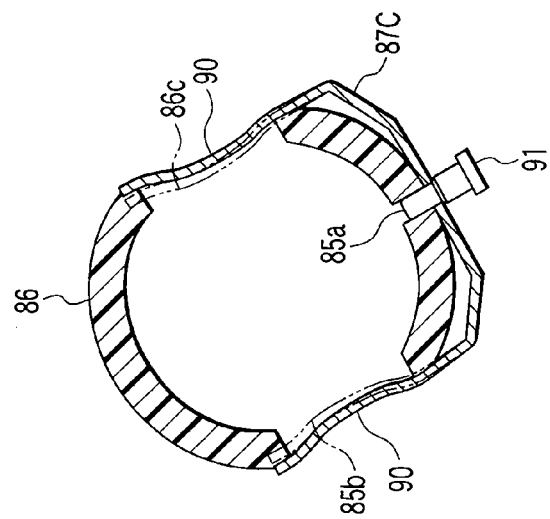
FIG. 21 is a cross-sectional view taken along line L21-L21 in FIG. 14.
Figure 22:
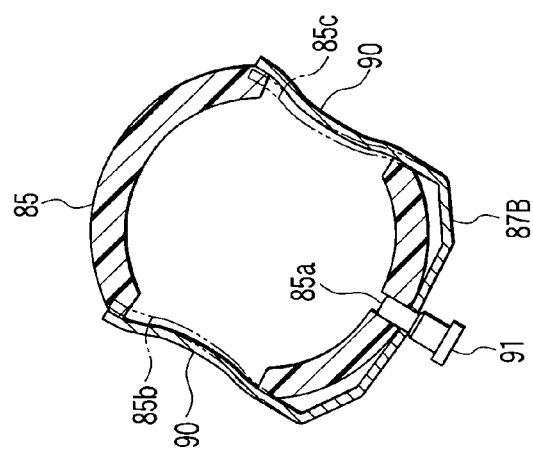
FIG. 22 is a cross-sectional view taken along line L22-L22 in FIG. 14.
Figure 23:
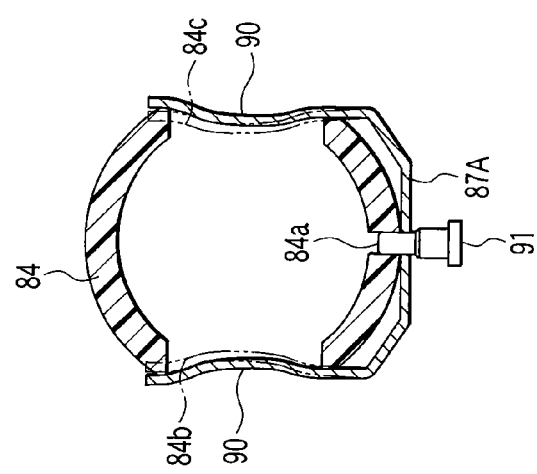
FIG. 23 is a cross-sectional view taken along line L23-L23 in FIG. 14.
Figure 24:
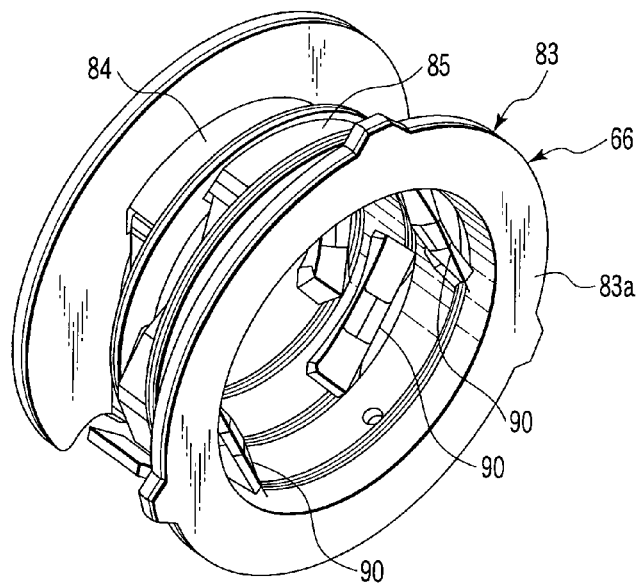
FIG. 24 is a perspective view showing an electrode hold member of the ultrasonic operating apparatus according to the first embodiment.
Figure 25:
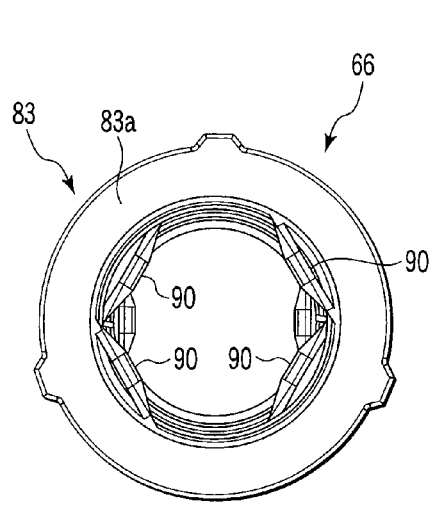
FIG. 25 is a front view showing the electrode hold member of the ultrasonic operating apparatus according to the first embodiment.
Figure 26:
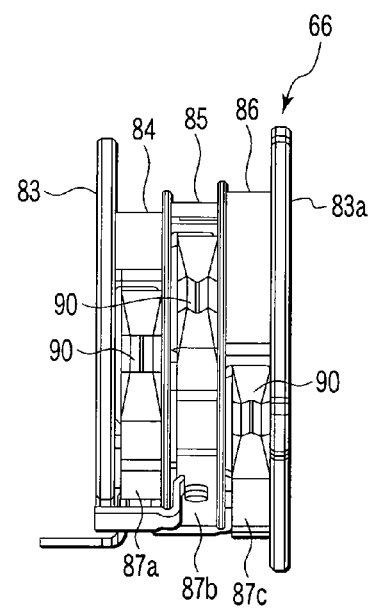
FIG. 26 is a side view showing the electrode hold member of the ultrasonic operating apparatus according to the first embodiment.

FIGS. 24 to 26 show the circular cylindrical contact-point unit 66. The contact-point unit 66 includes a circular cylindrical electrode hold member 83 which is formed of a resin. As shown in FIG. 26, the electrode hold member 83 includes three (first to third) electrode receiving sections 84, 85 and 86 with different outside diameters. The first electrode receiving section 84 on the distal end side has a smallest diameter, and the third electrode receiving section 86 on the rear end side has a greatest diameter. As shown in FIG. 21, the first electrode receiving section 84 has one contact-point member fixing hole 84a, and two through-holes 84b and 84c. A center line of the two through-holes 84b and 84c is set to be perpendicular to a center line of the contact-point member fixing hole 84a. Similarly, as shown in FIG. 22, the second electrode receiving section 85 has one contact-point member fixing hole 85a, and two through-holes 85b and 85c. As shown in FIG. 23, the third electrode receiving section 86 has one contact-point member fixing hole 86a, and two through-holes 86b and 86c.

The positions of the contact-point member fixing hole 85a of the first electrode receiving section 84, the contact-point member fixing hole 86a of the second electrode receiving section 85 and the contact-point member fixing hole 86a of the third electrode receiving section 86 are displaced in the circumferential direction of the electrode hold member 83.

FIG. 27 and FIG. 28 show electrode members 87A, 87B and 87C which are assembled to the first to third electrode receiving sections 84, 85 and 86. These electrode members 87A, 87B and 87C are formed in the same shape. In the description below, only the electrode member 87A, which is assembled to the first electrode receiving section 84, is described. The common parts of the electrode members 87B and 87C of the second and third electrode receiving sections 85 and 86 are denoted by like reference numerals, and a description thereof is omitted.

The electrode member 87A includes one straight stationary portion 87a and two bend portions 87b and 87c. One bend portion 87b is disposed at one end of the straight stationary portion 87a, and the other bend portion 87c is disposed at the other end of the straight stationary portion 87a. Thereby, as shown in FIG. 27, the electrode member 87A is formed and bent in a substantially U shape.

A hole 88 and an L-shaped wiring connection portion 89 are provided at a central position of the stationary portion 87a. Inwardly curved waist portions 90 are formed at central positions of the two bend portions 87b and 87c.

When the electrode member 87A is assembled to the first electrode receiving section 84, a fixing pin 91 is inserted in the hole 88 of the stationary portion 87a of the electrode member 87A and in the contact-point member fixing hole 85a of the first electrode receiving section 84. The electrode member 87A is fixed to the first electrode receiving section 84 by the fixing pin 91. At this time, the waist portion 90 of one bend portion 87b of the electrode member 87A is disposed in one through-hole 85b of the first electrode receiving section 84, and the waist portion 90 of the other bend portion 87c of the electrode member 87A is disposed in the other through-hole 85c. The same applies when the electrode member 87B is assembled to the second electrode receiving section 85 and the electrode member 87C is assembled to the third electrode receiving section 86.

As shown in FIG. 27, a large-diameter fixing flange portion 83a is formed at a rear end portion of the electrode hold member 83 of the contact-point unit 66. As shown in FIG. 20, engaging projection portions 83b are projectingly provided on the outer peripheral surface of the fixing flange portion 83a at a plurality of locations, for example, at three locations in this embodiment. Engaging recess portions 48a are formed in an inner peripheral surface of the rear end portion of the hold cylinder 48 at positions corresponding to the three engaging projection portions 83b of the fixing flange portion 83a. In the case where the electrode hold member 83 is assembled in the hold cylinder 48, the three engaging projection portions 83b of the fixing flange portion 83a are inserted, engaged and fixed in the engaging recess portions 48a of the hold cylinder 48. Thereby, the rotation of the electrode hold member 83 about the axis thereof, relative to the hold cylinder 48, is restricted.

A stepped portion 43b, which comes in contact with the fixing flange portion 83a of the electrode hold member 83, is formed on the hold cylinder 48. The electrode hold member 83 is fixed to the hold cylinder 48 by a fixing screw 48c in the state in which the fixing flange portion 83a of the electrode hold member 83 abuts upon the stepped portion 43b (see FIG. 14). Thereby, the axial movement of the electrode hold member 83, relative to the hold cylinder 48, is restricted.

End portions of three wiring lines 93a to 93c, which are assembled in the switch hold section 51, are connected to the wiring connection portions 89 of the three electrode members 87A, 87B and 87C that are assembled to the contact-point unit 66.

Further, as shown in FIG. 19, the contact-point unit 66 is provided with a substantially C-shaped electric contact-point member 96 which is formed of a metallic plate spring. The electric contact-point member 96 is connected to the outer-peripheral surface of the proximal end portion of the spring receiving member 64.

The handle-unit-side electric path 95 is composed of the electric contact-point member 96, spring receiving member 64, positioning pin 81 and rotation transmission member 71.

Figure 15B:
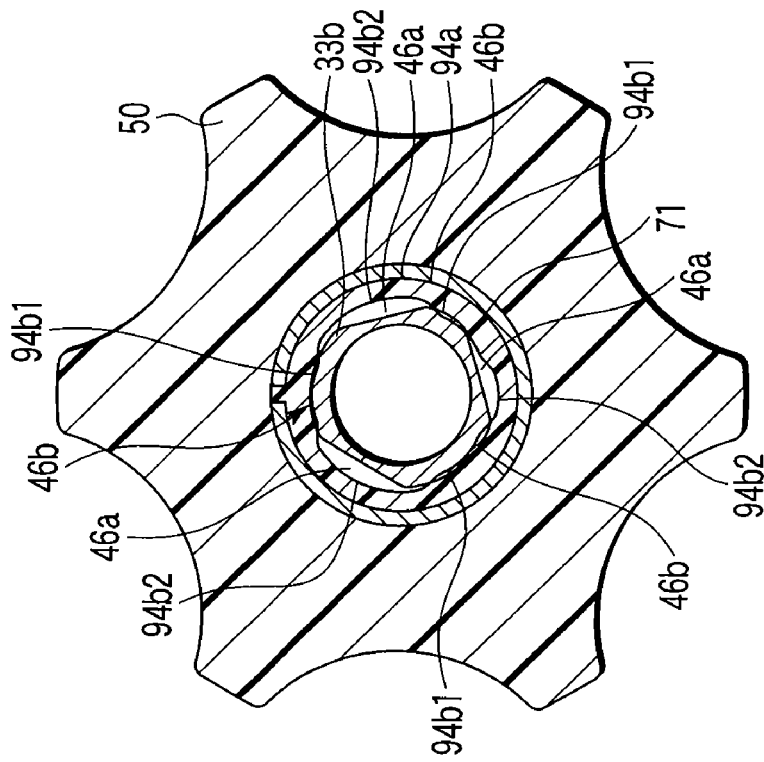
FIG. 15B is a longitudinal cross-sectional view showing a state after engagement between the handle unit and the sheath unit at the cross-sectional position along line L15A-L15A in FIG. 14.
Figure 15A:
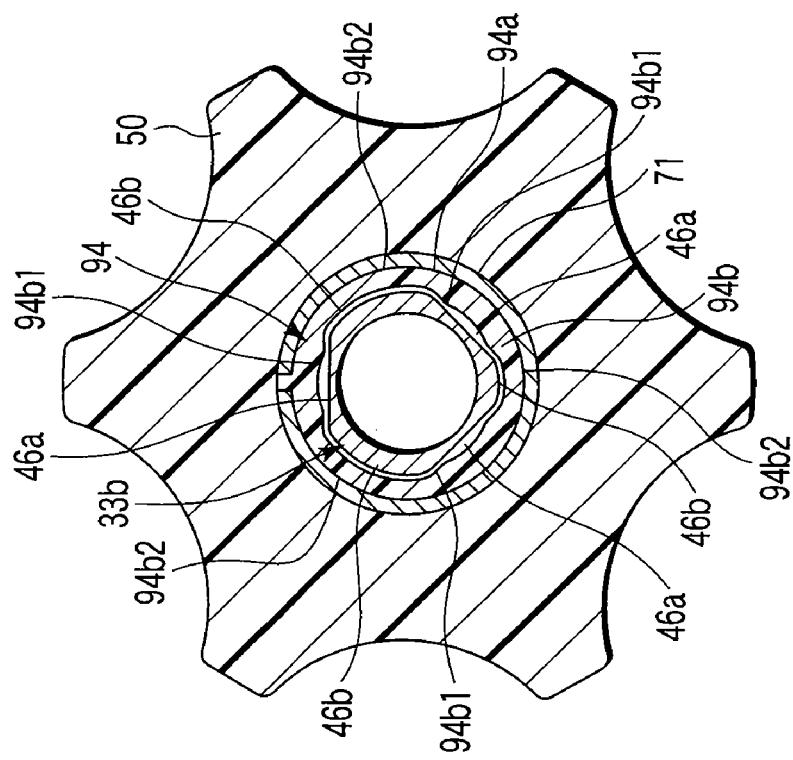
FIG. 15A is a longitudinal cross-sectional view showing a state before engagement between the handle unit and the sheath unit at a cross-sectional position along line L15A-L15A in FIG. 14.
Figure 16:
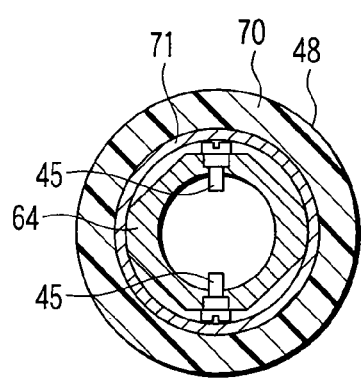
FIG. 16 is a cross-sectional view taken along line L16-L16 in FIG. 14.

Engaging means 94, which is disengageably engaged with the outer peripheral flange portion 33b of the sheath unit 5, is provided on the inner peripheral surface of the rotation transmission member 71 at a substantially central position in the axial direction. As shown in FIGS. 15A and 15B, the engaging means 94 includes an insertion hole portion 94a in which the outer peripheral flange portion 33b is inserted when the sheath unit 5 and handle unit 4 are coupled, and an electrically conductive rubber ring (urging means) 94b which is disposed within the insertion hole portion 94a.

The shape of the inner peripheral surface of the electrically conductive rubber ring 94b is substantially the same as the shape of the engaging portion 46 of the outer peripheral flange portion 33b. Specifically, the inner peripheral surface of the electrically conductive rubber ring 94b has three cut-out flat-surface portions 94b1 at a plurality of locations on the circular inner peripheral surface, for example, at three locations in this embodiment, and three corner portions 94b2 which are located at connection parts between the three flat-surface portions 94b1 and have greater diameters than the flat-surface portions 94b1. Thereby, the electrically conductive rubber ring 94b has a substantially triangular cross-sectional shape. Thus, as shown in FIG. 15A, the electrically conductive rubber ring 94b is held in a natural, non-compressed position in the positional state in which the inner peripheral surface shape of the electrically conductive rubber ring 94b corresponds to the engaging portion 46 of the outer peripheral flange portion 33b, that is, in the state in which the three corner portions 46b of the outer peripheral flange portion 33b correspond in position to the three corner portions 94b2 of the electrically conductive rubber ring 94b. On the other hand, by rotating the handle unit 4 and the sheath unit 5 relative to each other about the center axis of the sheath unit 5, the position of the electrically conductive rubber ring 94b is switched to a pressure contact position, as shown in FIG. 15B, where the electrically conductive rubber ring 94b is pressed on the three corner portions 46b of the outer peripheral flange portion 33b. At this time, the three corner portions 46b of the outer peripheral flange portion 33b are put in contact with, and pressed by, the three flat-surface portions 94b1 of the electrically conductive rubber ring 94b.

In the present embodiment, at the time of coupling the sheath unit 5 and handle unit 4, when the outer peripheral flange portion 33b of the sheath unit 5 is inserted straight into the electrically conductive rubber ring 94b (see FIG. 29 and FIG. 30), the electrically conductive rubber ring 94b is held in the natural, non-compressed position, as shown in FIG. 15A. At this time, the engaging lever 43 on the handle unit 4 side is held in the state in which the engaging lever 43 rests on the inclined surface of the guide groove 41 of the knob member 32 of the sheath unit 5. Subsequently, the knob member 32 of the sheath unit 5 is rotated about the axis, relative to the handle unit 4. Thereby, as shown in FIG. 31 and FIG. 32, the engaging lever 43 on the handle unit 4 side is inserted and engaged in the engaging recess portion 42 at one end portion of the guide groove 41. At this time, as shown in FIG. 15B, the electrically conductive rubber ring 94b is switched to the pressure contact position where the electrically conductive rubber ring 94b is put in pressure contact with the three corner portions 46b of the outer peripheral flange portion 33b. Thereby, a sheath-unit-side electric path 40 (formed between the guide cylindrical body 33, fixing screw 39, coupling pipe 38, outer cylinder 18, distal end cover 25, support pin 27 and jaw body 28) and a handle-unit-side electric path 95 (formed between the electric contact-point member 96, spring receiving member 64, positioning pin 81 and rotation transmission member 71) are electrically connected via the electrically conductive rubber ring 94b. In this case, a second high-frequency electric path 97, which transmits a high-frequency current, is formed in the coupled body of the sheath unit 5 and handle unit 4.

As shown in FIG. 19, the handle unit 4 includes a tubular member 98 which is formed of an insulating material on the inner peripheral surface of the spring receiving member 64.

The tubular member 9 is fixed on the inner peripheral surface of the spring receiving member 64. Thereby, when the probe unit 3 and the handle unit 4 are connected, the first high-frequency electric path 13 and the second high-frequency electric path 97 are insulated by the tubular member 98. An inner peripheral surface of the tubular member 98 has three engaging projection portions 99 which correspond to the three engaging recess portions 15 (see FIG. 35) of the flange portion 14 of the probe unit 3. When the probe unit 3 and handle unit 4 are connected, the three engaging projection portions 99 of the tubular member 98 are disengageably engaged with the three engaging recess portions 15 of the flange portion 14 of the probe unit 3. Thereby, the rotational-directional position between the probe unit 3 and the tubular member 98 of the handle unit 4 is restricted. Hence, when the rotational operation knob 50 is rotated, the coupled body of the probe unit 3 and transducer unit 2 is rotated as one body together with the assembly unit within the hold cylinder 48.

The engaging section between the flange portion 14 of the probe unit 3 and the tubular member 98 is not limited to the above-described structure. For example, the tubular member 98 may be formed to have a D-shaped cross section, and the flange portion 14 of the probe unit 3 may be formed to have a corresponding D-shaped cross section.

Figure 40:
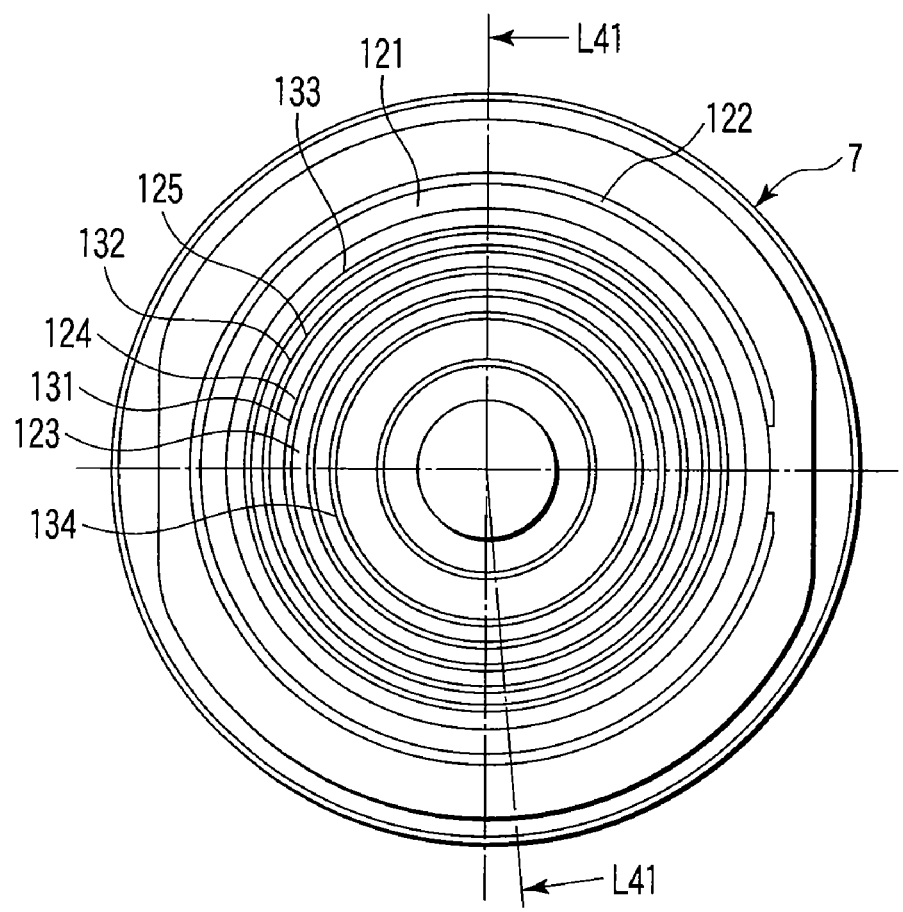
FIG. 40 is a front view showing a distal end portion of the transducer unit of the ultrasonic operating apparatus according to the first embodiment.

A front end portion of the transducer unit 2 is detachably coupled to the contact-point unit 66. As shown in FIG. 40, two wiring lines 101 and 102 for the ultrasonic transducer, two wiring lines 103 and 104 for conduction high-frequency electricity and three wiring lines 105, 106 and 107, which are connected to a wiring circuit board 92 within the switch hold section 51, are assembled in the single cable 9 at the rear end of the transducer unit 2. Distal end portions of the two wiring lines 101 and 102 for the ultrasonic transducer are connected to the ultrasonic transducer 6. A distal end portion of one wiring line 103 for conduction of high-frequency electricity is connected to the ultrasonic transducer 6.

FIG. 41 shows an internal structure of a front end portion of the transducer unit 2, and FIG. 42 shows an internal structure of a rear end portion of the transducer unit 2. The transducer cover 7 mainly includes a circular cylindrical storing section 211 and a cylindrical casing section 212. The storing section 211 is formed of a resin material that is an insulator, and stores the ultrasonic transducer 6. The casing section 212 is formed of a resin material that is an insulator, and is provided on the outside of the storing section 211.

As shown in FIG. 41, a ring-shaped transducer attachment member 213 is fixed on an inner peripheral surface of a distal end portion of the storing section 211. The ultrasonic transducer 6 is provided with a transducer flange 6a, which has a larger diameter than other parts, at a coupling end portion for coupling to a proximal end portion of the horn 10 on the probe unit 3 side. The transducer flange 6a is abutted and fixed on the transducer attachment member 213 of the storing section 211. A seal ring 214 is provided between the transducer attachment member 213 and the transducer flange 6a.

A distal end portion of the transducer attachment member 213 has a small-diameter extension portion 301 which extends into the inside of a connection cylindrical portion 121. A first O ring 215 is mounted on an inner peripheral surface of the extension portion 301, which comes in contact with the ultrasonic transducer 6. Thereby, a watertight part of the distal end portion of the transducer attachment member 213 is positioned forward, and thus the efficiency in cleaning of the distal end portion of the transducer attachment member 213 can be improved. A second O ring 216 is mounted on an outer peripheral surface of a proximal end portion of the transducer attachment member 213, which comes in contact with the inner peripheral surface of the storing section 211.

As shown in FIG. 42, a closing wall 211a for closing the proximal end side of the storing section 211 is formed on the proximal end side of the storing section 211. Three wiring line connection portions 217 for connection to some of wiring lines in the cable 9, namely, two wiring lines 101 and 102 for the ultrasonic transducer and one wiring line 103 for conduction of high-frequency electricity (see FIG. 48), are formed in a part of the closing wall 211a. As shown in FIG. 42, the respective wiring line connection portions 217 are sealed by sealing members 218.

Figure 44:
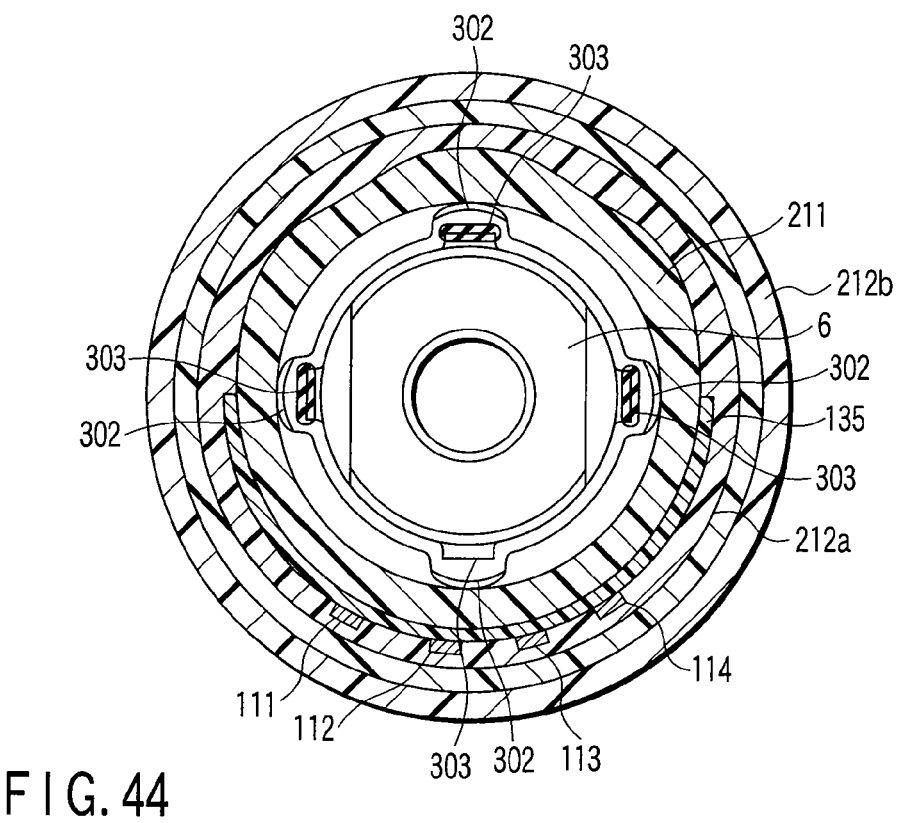
FIG. 44 is a cross-sectional view taken along line L44-L44 in FIG. 42.
Figure 45:
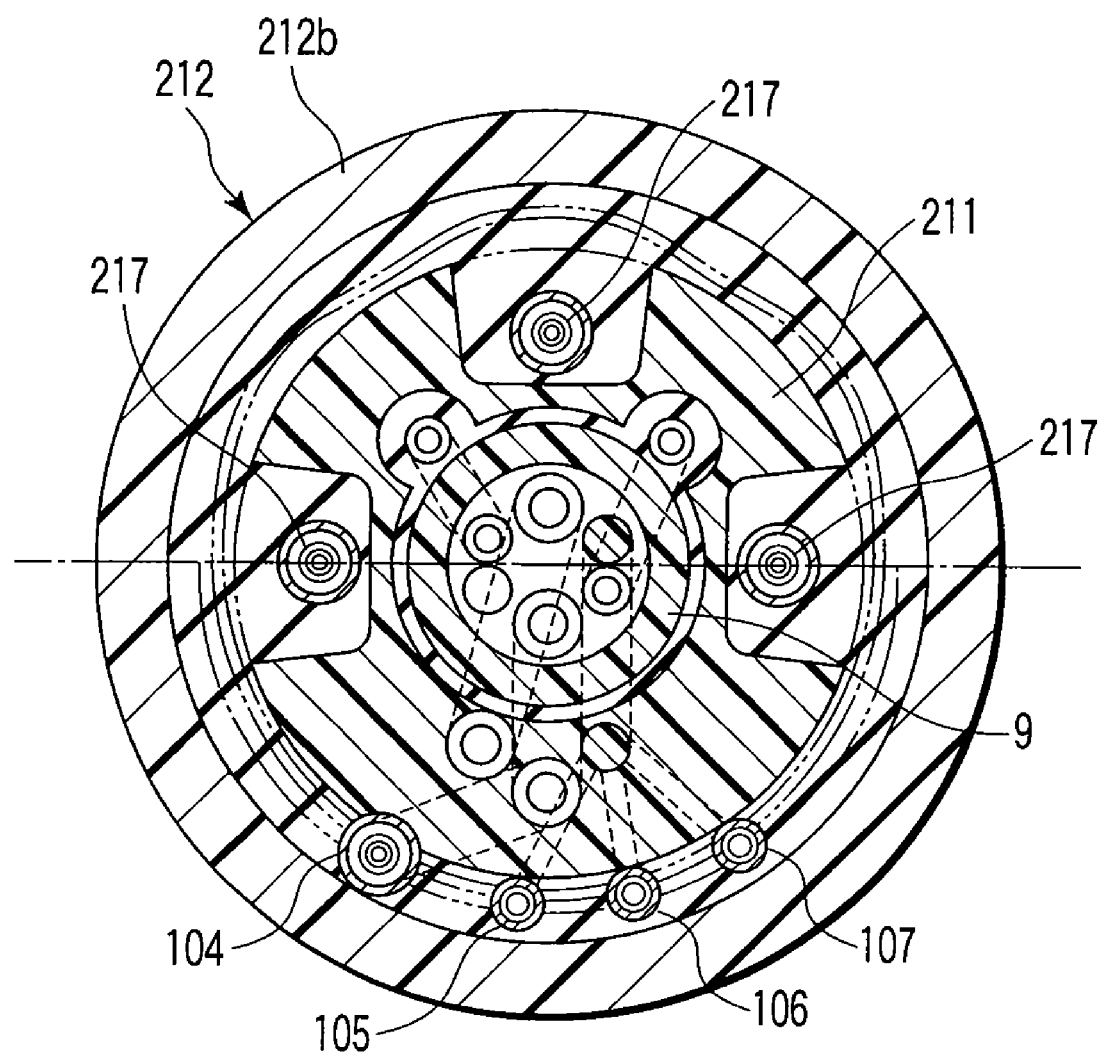
FIG. 45 is a cross-sectional view taken along line L45-L45 in FIG. 42.

As shown in FIG. 44, a plurality of engaging recess portions 302 are formed in an inner peripheral surface of the storing section 211. Each of the engaging recess portions 302 is formed in an arcuate shape. Flanges 303 of the ultrasonic transducer 6 are inserted and engaged in the engaging recess portions 302. By forming the arcuate shape for preventing rotation structures of the flanges 303 of the ultrasonic transducer 6, the machining is facilitated and the cost can advantageously be reduced.

The casing section 212 includes a front-side casing 212a shown in FIG. 41, and a rear-side casing 212b shown in FIG. 42. The connection cylindrical portion 121 is formed at a distal end portion of the front-side casing 212a. A C ring 122 having a partly cut-out and plate spring shape is mounted on the outer peripheral surface of the connection cylindrical body 121. A stepwise contact-point receiving section 126, which is formed to have an outside diameter decreasing stepwise toward its distal end, is formed inside the connection cylindrical portion 121. The contact-portion receiving section 126 projects forward from the distal end of the connection cylindrical portion 121 and includes three (from first to third) cylindrical portions from 123 to 125 with different outside diameters.

The first cylindrical portion 123 has a smallest outside diameter and has a greatest length of projection from the distal end of the connection cylindrical body 121. The second cylindrical portion 124 has an outside diameter, which is greater than the outside diameter of the first cylindrical portion 123, and has a length of projection from the distal end of the connection cylindrical body 121, which is less than the length of projection of the first cylindrical portion 123. The third cylindrical portion 125 has a greatest outside diameter and has a length of projection from the distal end of the connection cylindrical body 121, which is less than the length of projection of the second cylindrical portion 124.

Figure 46:
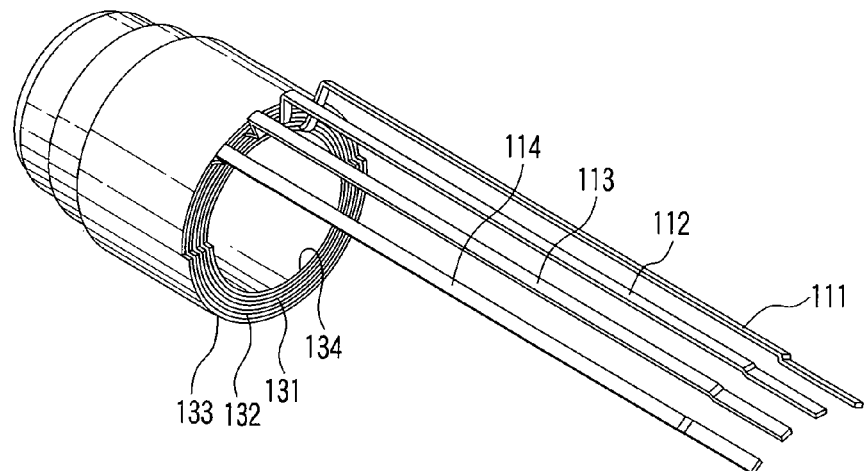
FIG. 46 is a perspective view showing an arrangement state of contact-point members and conductive plates of the transducer unit of the ultrasonic operating apparatus according to the first embodiment.
Figure 47:
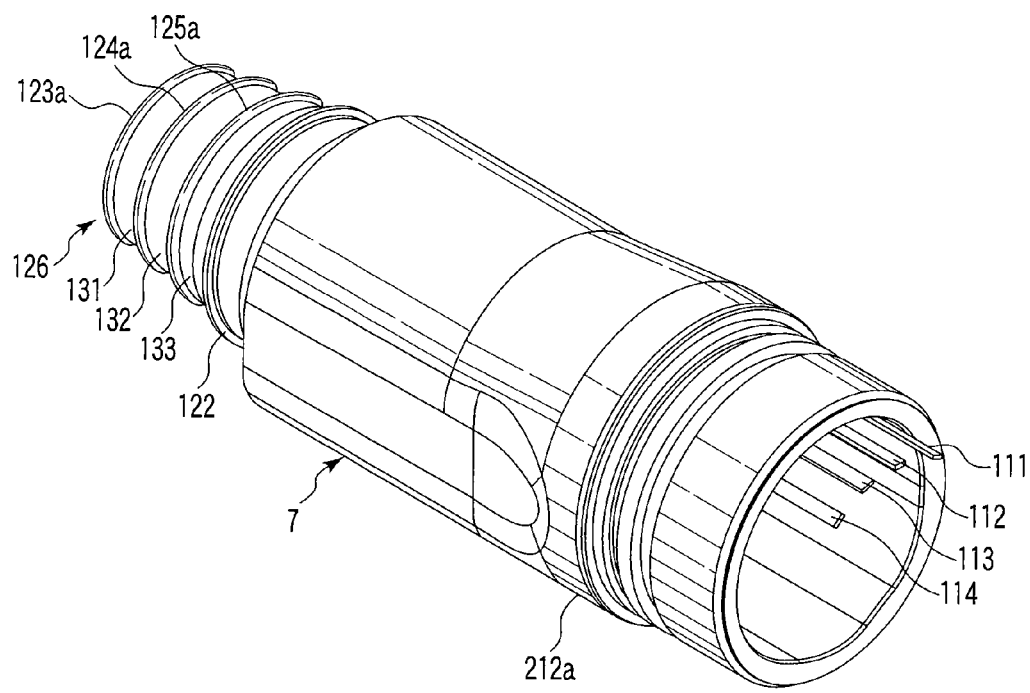
FIG. 47 is a perspective view showing a casing of the transducer unit of the ultrasonic operating apparatus according to the first embodiment.
Figure 48:
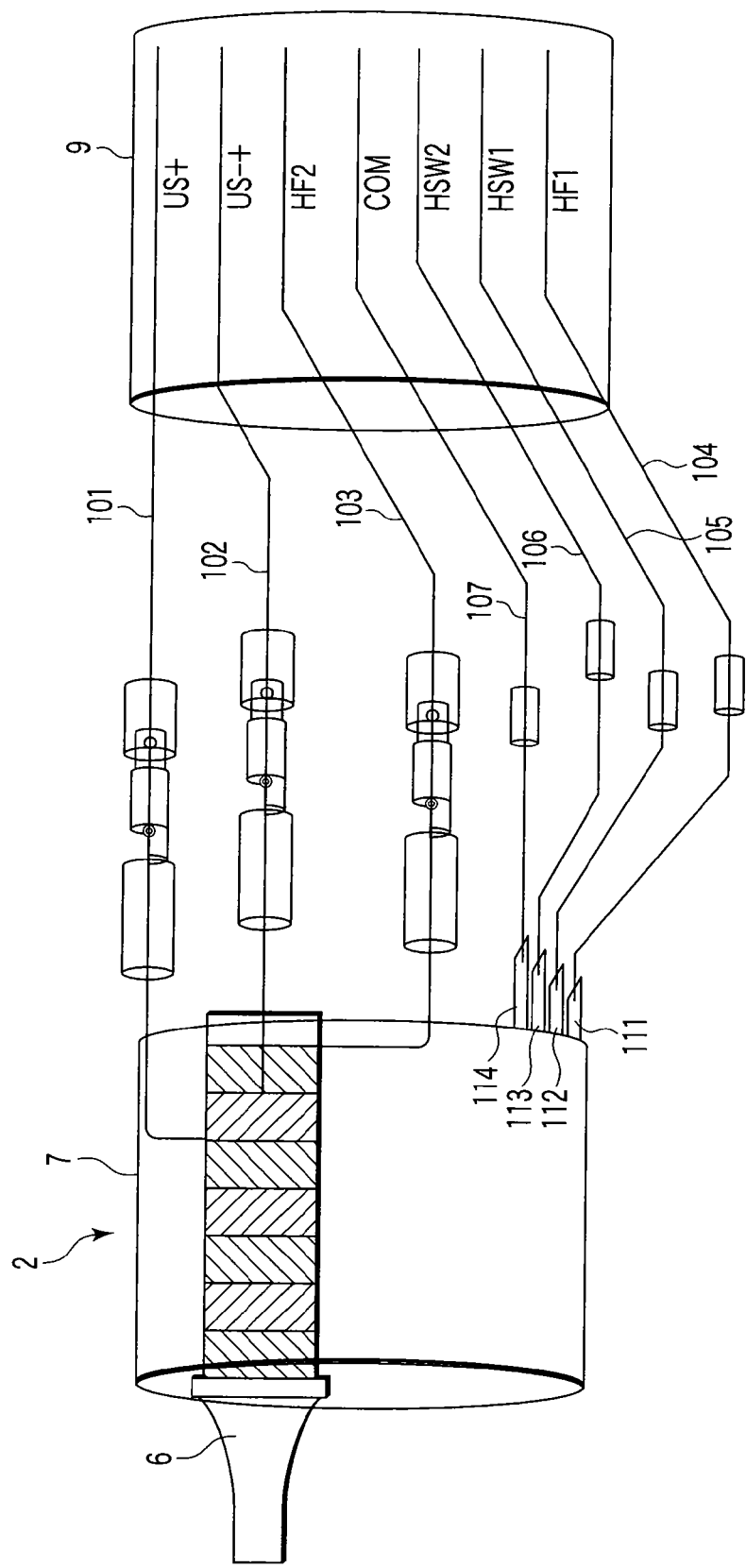
FIG. 48 is a schematic view showing the structure of an electric path of the transducer unit of the ultrasonic operating apparatus according to the first embodiment.

A first cylindrical contact-point member 131 is mounted on the outer peripheral surface of the first cylindrical portion 123. Similarly, a second cylindrical contact-point member 132 is mounted on the outer peripheral surface of the second cylindrical portion 124, and a third cylindrical contact-point member 133 is mounted on the outer peripheral surface of the third cylindrical portion 125. As shown in FIG. 46, a flat-plate-shaped second electrically conductive plate (electrical path element) 112 for electrical connection is connected to the first contact-point member 131. A flat-plate-shaped third electrically conductive plate (electrical path element) 113 is connected to the second contact-point member 132. A flat-plate-shaped fourth electrically conductive plate (electrical path element) 114 is connected to the third contact-point member 133. A circular cylindrical fourth contact-point member 134 is mounted on an inner peripheral surface of the first cylindrical portion 123. The fourth contact-point member 134 is connected to a first electrically conductive plate (electrical path element) 111.

Figure 43:
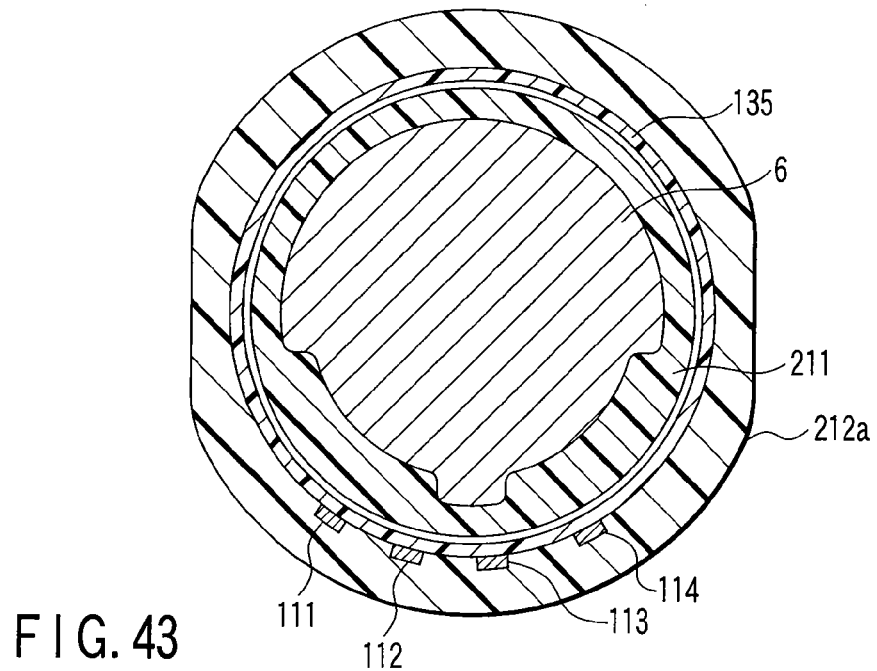
FIG. 43 is a cross-sectional view taken along line L43-L43 in FIG. 41.

The first electrically conductive plate 111, second electrically conductive plate 112, third electrically conductive plate 113 and fourth electrically conductive plate 114 extend substantially straight in parallel to the center axis of the casing section 212 toward the proximal end side of the storing section 211. As shown in FIGS. 43 and 44, the four electrically conductive plates 111 to 114 are juxtaposed in the circumferential direction on the parts of the same diameter, relative to the center axis of the transducer 6. The four electrically conductive plates 111 to 114 are buried in the inner peripheral surface of the front-side casing 212a and are molded integral with the front-side casing 212a. Thereby, the four electrically conductive plates 111 to 114 are disposed between the front-side casing 212a and the storing section 211.

A resin-made circular cylindrical member 135 is provided on the outer peripheral surface of the distal end portion of the storing section 211. A distal end portion of the circular cylindrical member 135 is bent along the inner peripheral surface of the contact-point receiving section 126 and is made to extend toward the inner peripheral side of the fourth contact-point member 134. A third O ring 219 is mounted on the outer peripheral surface of the distal end portion of the storing section 211, which comes in contact with the circular cylindrical member 135.

A ring-shaped small-diameter portion 212a1 is formed on the outer peripheral surface of the proximal end portion of the front-side casing 212a. A distal end portion of the rear-side casing 212b is fitted over and coupled to the small-diameter portion 212a1. A fourth O ring 220 is mounted on the outer peripheral surface of the small-diameter portion 212a1 of the front-side casing 212a, which comes in contact with the rear-side casing 212b.

Proximal end portions of the first to fourth electrically conductive plates 111 to 114 extend onto the outer peripheral surface of the proximal end portion of the storing section 211. A distal end portion of the other wiring line 104 for conduction of high-frequency electricity is connected to the first electrically conductive plate 111. The three wiring lines 105, 106 and 107 are connected to the second to fourth electrically conductive plates 112 to 114.

A fifth O ring 221 is mounted on the inner peripheral surface of the proximal end portion of the rear-side casing 212b, which comes in contact with the cable 9. Thereby, the coupling part between the rear-side casing 212b and the cable 9 is sealed by the fifth O ring 221.

When the handle unit 4 and the transducer unit 2 are coupled, the contact-point unit 66 of the handle unit 4 and the front end portion of the transducer unit 2 are connected. At this time, the electrode member 87A of the contact-point unit 66 and the first contact-point member 131 of the transducer unit 2 are connected. At the same time, the electrode member 87B of the contact-point unit 66 and the second contact-point member 132 of the transducer unit 2 are connected, the electrode member 87C of the contact-point unit 66 and the third contact-point member 133 of the transducer unit 2 are connected, and the C-shaped electric contact-point member 96 of the contact-point unit 66 and the fourth contact-point member 134 of the transducer unit 2 are connected.

As shown in FIG. 49, in the present embodiment, a first projection portion 123a of an insulating material is provided in front of the first contact-point member 131 of the connection cylindrical portion 121. The first projection portion 123a projects radially outward from the same plane as the plane of the first contact-point member 131 at the distal end portion of the first cylindrical portion 123.

Similarly, a second projection portion 124a of an insulating material is provided in front of the second contact-point member 132 of the connection cylindrical portion 121. The second projection portion 124a projects radially outward from the same plane as the plane of the second contact-point member 132 at the distal end portion of the second cylindrical portion 124. Further, a third projection portion 125a of an insulating material is provided in front of the third contact-point member 133 of the connection cylindrical portion 121. The third projection portion 125a projects radially outward from the same plane as the plane of the third contact-point member 133 at the distal end portion of the third cylindrical portion 125.

The first projection portion 123a, second projection portion 124a and third projection portion 125a are formed integral with the first cylindrical portion 123, second cylindrical portion 124 and third cylindrical portion 125 of the connection cylindrical portion 121, respectively.

In addition, the first projection portion 123a, second projection portion 124a and third projection portion 125a are set to project radially outward, at least, from a straight line L1 which connects the distal end portions of the first contact-point member 131, second contact-point member 132 and third contact-point member 133.

Next, the operation of the present embodiment is described. The handpiece 1 of the ultrasonic operating apparatus of the present embodiment, as shown in FIG. 2, comprises four units, namely, the transducer unit 2, probe unit 3, handle unit 4 and sheath unit 5, which are detachable. When the handpiece 1 is used, the transducer unit 2 and the probe unit 3 are coupled. Thereby, the first high-frequency electric path 13, which transmits a high-frequency current to the coupled body of the transducer unit 2 and probe unit 3, is formed.

Subsequently, the handle unit 4 and the sheath unit 5 are coupled. When the handle unit 4 and sheath unit 5 are coupled, the connection tube body 34 is inserted in the rotation transmission member 71 of the handle unit 4 in the state in which the knob member 32 of the sheath unit 5 is held. When the sheath unit 5 and handle unit 4 are coupled, the engaging lever 43 on the handle unit 4 side is held in the state in which the engaging lever 43 runs on the inclined surface of the guide groove 41 of the knob member 32 of the sheath unit 5, as shown in FIG. 29 and FIG. 30. At this time, as shown in FIG. 15A, the electrically conductive rubber ring 94b is held in the positional state in which the inner peripheral surface shape of the electrically conductive rubber ring 94b corresponds to the engaging portion 46 of the outer peripheral flange portion 33b, that is, in the state in which the three corner portions 46b of the outer peripheral flange portion 33b correspond in position to the three corner portions 94b2 of the electrically conductive rubber ring 94b. Accordingly, the outer peripheral flange portion 33b of the sheath unit 5 is inserted straight into the electrically conductive rubber ring 94b. At the time of this insertion operation, as shown in FIG. 15A, the conductive rubber ring 94b is held in the natural, non-compressed position. In this state, the sheath-unit-side electric path 40 and the handle-unit-side electric path 95 are not electrically connected.

Subsequently, following this insertion operation, the knob member 32 of the sheath unit 5 is rotated about the axis thereof, relative to the handle unit 4. By this operation, as shown in FIG. 31 and FIG. 32, the engaging lever 43 on the handle unit 4 side is inserted and engaged in the engaging recess portion 42 at one end portion of the guide groove 41. At this time, as shown in FIG. 15B, the electrically conductive rubber ring 94b is switched to the pressure contact position where the electrically conductive rubber ring 94b is put in pressure contact with the three corner portions 46b of the outer peripheral flange portion 33b. Thereby, the sheath-unitside electric path 40 and the handle-unit-side electric path 95 are electrically connected via the electrically conductive rubber ring 94b. As a result, the second high-frequency electric path 97, which transmits a high-frequency current, is formed in the coupled body of the sheath unit 5 and handle unit 4.

When the sheath unit 5 is rotated about the axis thereof, the pair of engaging pins 45 on the handle unit 4 side are, at the same time, disengageably engaged in the engaging groove 44a at the terminal end portion of the guide groove 44 of the sheath unit 5. Thereby, the spring receiving member 64 on the handle unit 4 side and the connection tube body 34 on the sheath unit 5 side are coupled via the engaging pins 45. As a result, the operation force on the handle unit 4 side at the time when the movable handle 49 is closed relative to the stationary handle 47 can be transmitted to the driving shaft 21 of the jaw 17 on the sheath unit 5 side. This state is the coupled state between the sheath unit 5 and the handle unit 4.

Thereafter, the coupled body of the sheath unit 5 and handle unit 4 and the coupled body of the ultrasonic transducer 6 and probe unit 3 are assembled as one body. In this assembling work, the contact-point unit 66 of the handle unit 4 is connected to the front end portion of the transducer unit 2. At this time, the electrode member 87A of the contact-point unit 66 and the first contact-point member 131 of the transducer unit 2 are connected. At the same time, the electrode member 87B of the contact-point unit 66 and the second contact-point member 132 of the transducer unit 2 are connected, the electrode member 87C of the contact-point unit 66 and the third contact-point member 133 of the transducer unit 2 are connected, and the C-shaped electric contact-point member 96 of the contact-point unit 66 and the fourth contact-point member 134 of the transducer unit 2 are connected. Thereby, the second high-frequency electric path 97 of the coupled body of the sheath unit 5 and handle unit 4 is connected to the wiring line 104 for conduction of high-frequency electricity within the cable 9. Further, the three wiring lines 105, 106 and 107 within the cable 9 are connected to a wiring circuit board 503a within the switch hold section 51. This state is the completion state of the assembly of the handpiece 1.

When the handpiece 1 is used, the movable handle 49 and stationary handle 47 are grasped in the state in which the thumb is inserted in the thumb insertion ring portion 62 of the movable handle 49 and the plural fingers, other than the thumb and the first finger, are inserted in the plural finger insertion ring portion 61 of the stationary handle 47. In this state, the movable handle 49 is closed relative to the stationary handle 47. The driving shaft 21 is axially moved in interlock with the operation of the movable handle 4, and the jaw 17 is opened/closed, relative to the probe distal end portion 3a of the probe unit 3, in interlock with the advancing/retreating movement of the driving shaft 21 in its axial direction. Thereby, a living tissue is held between the jaw 17 and the probe distal end portion 3a of the probe unit 3.

In this state, one of the first switch button 54a and the second switch button 55a of the stationary handle 47 is selectively pressed. When the second switch button 55a is pressed, power is supplied to the first high-frequency electric path 13 for supplying a high-frequency current to the probe distal end portion 3a of the probe unit 3 and to the second high-frequency electric path 97 for supplying a high-frequency current to the jaw body 28 of the sheath unit 5. Thereby, the two bipolar electrodes for high-frequency therapeutic treatment are constituted by the probe distal end portion 3a of the probe unit 3 and the jaw body 28 of the sheath unit 5. By supplying a high-frequency current between the two bipolar electrodes which are constituted by the probe distal end portion 3a of the probe unit 3 and the jaw body 28 of the sheath unit 5, bipolar high-frequency therapeutic treatment can be performed on the living tissue between the jaw 17 and the probe distal end portion 3a of the probe unit 3.

When the first switch button 54a is pressed, a driving current is supplied to the ultrasonic transducer 6 at the same time as the supply of high-frequency current, and the ultrasonic transducer 6 is driven. At this time, ultrasonic vibration from the ultrasonic transducer 6 is transmitted to the probe distal end portion 3a via the vibration transmission member 11. Thereby, incision, resection, etc. of the living tissue can be performed by making use of ultrasonic waves at the same time as the supply of high-frequency current. In the meantime, coagulation for the living tissue can also be performed by using ultrasonic waves.

When the rotational operation knob 50 is rotated, the rotational movement of the rotation transmission member 71, which rotates together with the rotational operation knob 50, is transmitted to the spring receiving member 64 side via the pin 81. Thereby, when the rotational operation knob 50 is rotated, the assembly unit of the rotation transmission member 71, pin 81, spring receiving member 64, slider member 65 and coil spring 67 within the hold cylinder 48 is rotated together with the rotational operation knob 50 as one body about the axis thereof. Further, the rotational operation force of the rotational operation knob 50 is transmitted to the vibration transmission member 11 of the probe unit 3 via the tubular member 98 that rotates together with the spring receiving member 64 within the hold cylinder 48. Thereby, the assembly unit within the hold cylinder 48 and the coupled body of the transducer unit 2 and probe unit 3 are rotated together about the axis as one body.

The following advantageous effects can be obtained with the above-described structure. Specifically, in the handpiece 1 of the ultrasonic operating apparatus according to the present embodiment, the first projection portion 123a of an insulating material is provided in front of the first contact-point member 131 of the connection cylindrical portion 121 of the transducer unit 2. Similarly, the second projection portion 124a of an insulating material is provided in front of the second contact-point member 132 of the connection cylindrical portion 121. Further, the third projection portion 125a of an insulating material is provided in front of the third contact-point member 133 of the connection cylindrical portion 121. Thus, in the case where the transducer unit 2 is placed on a metallic table in the state in which the transducer unit 2 is separated from the handle unit 4, the first projection portion 123a, second projection portion 124a and third projection portion 125a, which are formed of insulate material, necessarily come in contact with the metallic table before the first contact-point member 131, second contact-point member 132 and third contact-point member 133, which are formed of a metallic material, come in contact with the metallic surface of the metallic table. As a result, the electrode members, such as the first contact-point member 131, second contact-point member 132 and third contact-point member 133, which are formed of a metallic material, are not damaged due to contact with the metallic table. Moreover, it is possible to prevent occurrence of electric short-circuit between the metallic table, on the one hand, and the electrode members, such as the first contact-point member 131, second contact-point member 132 and third contact-point member 133, on the other hand.

FIG. 50 shows a second embodiment of the present invention. In this embodiment, the structure of the connection cylindrical portion 121 of the transducer unit 2 of the first embodiment is altered as follows. Specifically, in the present embodiment, the second projection portion 124a of the insulating material, which is provided in front of the second contact-point member 132 of the connection cylindrical portion 121, is replaced with a flat smooth surface 124z of the second cylindrical portion 124. The flat smooth surface 124z is formed by providing an annular peripheral surface, which is flush with the second contact-point member 132, in front of the second contact-point member 132 of the connection cylindrical portion 121.

The following advantageous effect can be obtained with this structure. Specifically, in this embodiment, the annular flat smooth surface 124z, which is flush with the second contact-point member 132, is provided in front of the second contact-point member 132 of the connection cylindrical portion 121. Therefore, in the case where the connection cylindrical portion 121 of the transducer unit 2 is formed of an insulating material by molding as one body with the first to third contact-point members 131 to 133, the structure of the die for molding can be simplified. As a result, the manufacturing cost of the transducer unit 2 can be reduced.

FIG. 51 shows a third embodiment of the present invention. In this embodiment, the structure of the connection cylindrical portion 121 of the transducer unit 2 of the first embodiment is altered as follows. Specifically, in the present embodiment, taper surfaces 123b, 124b and 125b are provided, respectively, on the outer peripheral surfaces of distal end portions of the first projection portion 123a in front of the first contact-point member 131, the second projection portion 124a in front of the second contact-point member 132, and the third projection portion 125a in front of the third contact-point member 133.

The following advantageous effect can be obtained with this structure. Specifically, in this embodiment, when the transducer unit 2 and handle unit 4 are to be connected, the connection cylindrical portion 121 of the transducer unit 2 can smoothly be inserted into the hold cylinder 48 of the handle unit 4 by the taper surfaces 123b, 124b and 125b which are provided on the outer peripheral surfaces of the distal end portions of the first projection portion 123a, the second projection portion 124a and the third projection portion 125a. Therefore, the work for connection between the transducer unit 2 and handle unit 4 can be facilitated.

Figure 52:
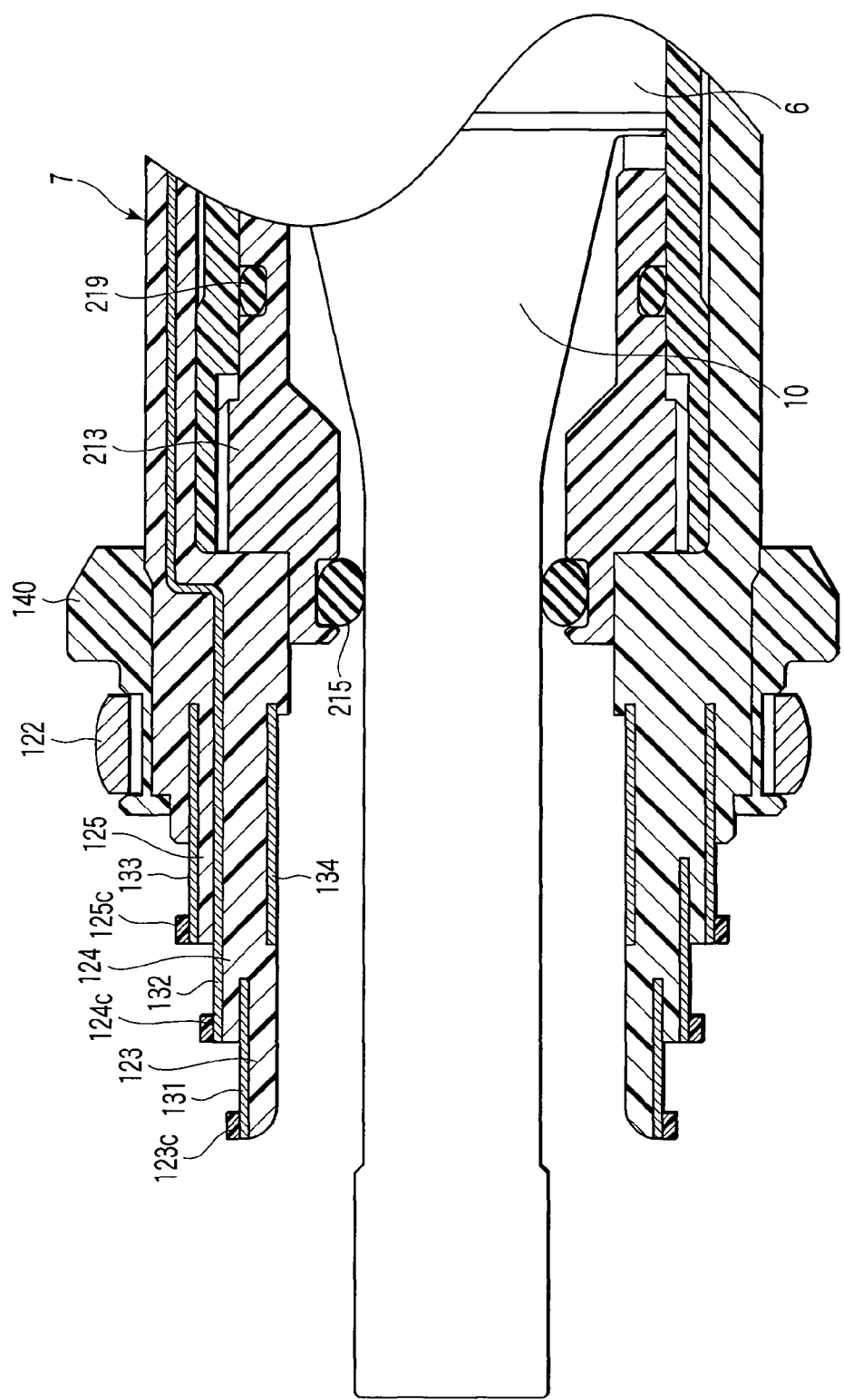
FIG. 52 is a longitudinal cross-sectional view showing a connection circular cylindrical portion of a transducer unit of an ultrasonic operating apparatus according to a fourth embodiment of the present invention.

FIG. 52 shows a fourth embodiment of the present invention. In this embodiment, the structure of the connection cylindrical portion 121 of the transducer unit 2 of the first embodiment is altered as follows. Specifically, in the present embodiment, a first insulating ring 123c, which is an external member and is formed of an insulating material different from the material of the first cylindrical portion 123 of the connection cylindrical portion 121, is laid and fixed on a front part of the first contact-point member 131. Similarly, a second insulating ring 124c, which is an external member and is formed of an insulating material different from the material of the second cylindrical portion 124 of the connection cylindrical portion 121, is laid and fixed on a front part of the second contact-point member 132. Further, a third insulating ring 125c, which is an external member and is formed of an insulating material different from the material of the third cylindrical portion 125 of the connection cylindrical portion 121, is laid and fixed on a front part of the third contact-point member 133. The first to third insulating rings 123c to 125c may be, for instance, heat-shrinkable tubes.

The following advantageous effect can be obtained with this structure. Specifically, in this embodiment, the work for providing projection portions at the front parts of the first to third contact-point members 131 to 133 can be facilitated.

FIG. 53 shows a fifth embodiment of the present invention. In this embodiment, the structure of the connection cylindrical portion 121 of the transducer unit 2 of the first embodiment is altered as follows. Specifically, in the present embodiment, a first insulating coating 123d, which is formed of an insulating material different from the material of the first cylindrical portion 123 of the connection cylindrical portion 121, is provided by coating on a front part of the first contact-point member 131. Similarly, a second insulating coating 124d, which is formed of an insulating material different from the material of the second cylindrical portion 124 of the connection cylindrical portion 121, is provided by coating on a front part of the second contact-point member 132. Further, a third insulating coating 125d, which is formed of an insulating material different from the material of the third cylindrical portion 125 of the connection cylindrical portion 121, is provided by coating on a front part of the third contact-point member 133.

The following advantageous effect can be obtained with this structure. Specifically, in this embodiment, the work for providing projection portions at the front parts of the first to third contact-point members 131 to 133 can be facilitated.

Needless to say, the present invention is not limited to the above-described embodiments, and can be variously modified and embodied without departing from the spirit of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic transducer unit configured to be attached to and detached from a handle section including at least one contact-point, the ultrasonic transducer unit comprising:
   an ultrasonic transducer configured to generate ultrasonic vibration;
   a transducer cover including a storing section which stores the ultrasonic transducer;
   a connection cylindrical portion disposed to a distal end of the transducer cover and adapted to be attached to and detached from the handle section;
   at least one electric contact portion provided on an outer peripheral surface of the connection cylindrical portion and being in a conductive connection with the contact-point of the handle section when the ultrasonic transducer unit is connected to the handle section; and
   at least one insulative projection portion provided on the connection cylindrical portion and provided at a distal end side of the electric contact portion and projects more radially outward than an outer peripheral surface of the electric contact portion.

2. The transducer unit according to claim 1, wherein
   the connection cylindrical portion includes a plurality of cylindrical sections having different outside diameters and different lengths of projection from the distal end of the transducer cover,
   the at least one electric contact portion is provided on the outer peripheral surface of the cylindrical section of the connection cylindrical portion, and
   the at least one insulative projection portion is provided at a distal end of the cylindrical section.

3. The transducer unit according to claim 2, wherein
the plurality of cylindrical sections have at least three cylindrical sections, and
the at least one insulative projection portion is provided on the cylindrical section having a smallest diameter and the cylindrical section having a largest diameter.

4. The transducer unit according to claim 1, wherein the at least one insulative projection portion is provided with a taper surface formed on an outer peripheral surface.

5. The transducer unit according to claim 1, wherein the at least one insulative projection portion includes an insulative stationary ring which is fixed on an outer peripheral surface of a distal end portion of the electric contact portion.

6. The transducer unit according to claim 1, wherein the at least one insulative projection portion includes an insulative coating portion which is coated on an outer peripheral surface of a distal end portion of the electric contact portion.

* * * * *